United States Patent
Lashkari

(10) Patent No.: US 10,117,931 B2
(45) Date of Patent: Nov. 6, 2018

(54) METHODS FOR TREATMENT OF AGE-RELATED MACULAR DEGENERATION

(71) Applicant: Kameran Lashkari, Boston, MA (US)

(72) Inventor: Kameran Lashkari, Boston, MA (US)

(73) Assignee: Kameran Lashkari, Boston, MA (US)

( * ) Notice: Subject to any disclaimer, the term of this patent is extended or adjusted under 35 U.S.C. 154(b) by 19 days.

(21) Appl. No.: 14/134,633

(22) Filed: Dec. 19, 2013

(65) Prior Publication Data

US 2014/0120112 A1 May 1, 2014

Related U.S. Application Data

(60) Division of application No. 13/283,739, filed on Oct. 28, 2011, now abandoned, which is a continuation-in-part of application No. PCT/US2010/032801, filed on Apr. 28, 2010.

(60) Provisional application No. 61/287,248, filed on Dec. 17, 2009, provisional application No. 61/173,257, filed on Apr. 28, 2009.

(51) Int. Cl.

| | |
|---|---|
| *A61K 38/00* | (2006.01) |
| *A61K 38/17* | (2006.01) |
| *A61K 39/395* | (2006.01) |
| *A61K 31/40* | (2006.01) |
| *A61K 31/69* | (2006.01) |
| *A61K 31/216* | (2006.01) |
| *A61K 31/351* | (2006.01) |
| *A61K 31/445* | (2006.01) |
| *A61K 31/519* | (2006.01) |
| *A61K 31/4545* | (2006.01) |
| *A61K 31/5375* | (2006.01) |
| *C07K 14/715* | (2006.01) |
| *C07K 16/28* | (2006.01) |
| *G01N 33/68* | (2006.01) |

(52) U.S. Cl.
CPC ........ *A61K 39/3955* (2013.01); *A61K 31/216* (2013.01); *A61K 31/351* (2013.01); *A61K 31/40* (2013.01); *A61K 31/445* (2013.01); *A61K 31/4545* (2013.01); *A61K 31/519* (2013.01); *A61K 31/5375* (2013.01); *A61K 31/69* (2013.01); *C07K 14/7158* (2013.01); *C07K 16/28* (2013.01); *G01N 33/6863* (2013.01); *G01N 33/6866* (2013.01); *C07K 2317/76* (2013.01); *G01N 2333/4715* (2013.01); *G01N 2333/521* (2013.01); *G01N 2800/16* (2013.01); *G01N 2800/50* (2013.01)

(58) Field of Classification Search
CPC .. A61K 39/3955; A61K 39/505; A61K 45/06; A61K 38/00; A61K 31/69; A61K 31/5375; A61K 31/519; A61K 31/4545; A61K 31/40; A61K 31/351; A61K 31/216; A61K 31/445; A61K 38/179; C07K 16/28; C07K 14/7158

See application file for complete search history.

(56) References Cited

U.S. PATENT DOCUMENTS

| | | |
|---|---|---|
| 5,643,893 A | 7/1997 | Benson et al. |
| 6,140,064 A | 10/2000 | Loetscher et al. |
| 6,184,358 B1 | 2/2001 | Loetscher et al. |
| 6,331,541 B1 | 12/2001 | Ko et al. |
| 6,521,592 B2 | 2/2003 | Ko et al. |
| 6,559,160 B1 | 5/2003 | Schall et al. |
| 6,566,376 B1 | 5/2003 | Baxter et al. |
| 6,627,629 B2 | 9/2003 | Ko et al. |
| 6,686,175 B1 | 2/2004 | Loetscher et al. |
| 6,706,735 B2 | 3/2004 | Watson et al. |
| 6,759,411 B2 | 7/2004 | Ko et al. |
| 6,780,857 B2 | 8/2004 | Ko et al. |
| 6,821,964 B2 | 11/2004 | Colon-Cruz et al. |
| 6,864,380 B2 | 3/2005 | Wacker et al. |
| 6,875,776 B2 | 4/2005 | Ko et al. |
| 6,897,234 B2 | 5/2005 | Ko et al. |
| 6,903,115 B2 | 6/2005 | Rigby et al. |
| 6,906,066 B2 | 6/2005 | Ko et al. |
| 6,919,368 B2 | 7/2005 | Ko et al. |
| 6,949,546 B2 | 9/2005 | Ko et al. |
| 6,960,666 B2 | 11/2005 | Duncia et al. |
| 6,974,869 B2 | 12/2005 | DeLucca |
| 6,984,643 B2 | 1/2006 | Du Bois et al. |
| 6,984,651 B2 | 1/2006 | Duncia et al. |
| 6,992,084 B2 | 1/2006 | Schall et al. |
| 7,029,862 B1 | 4/2006 | Loetscher et al. |
| 7,091,310 B2 | 8/2006 | Merzouk et al. |

(Continued)

FOREIGN PATENT DOCUMENTS

| | | |
|---|---|---|
| DE | 19837386 A1 | 2/1999 |
| EP | 1013276 A1 | 6/2000 |

(Continued)

OTHER PUBLICATIONS

Fife, B.T. et al. CXCL-10 (IFN-g-inducible protein-10) control of encephalitogenic CD4+ T cell accumulation in the central nervous system during experimental autoimmune encephalomyelitis. J. Immunol, 2001, vol. 166, p. 7617-7624.*

Fujimura, S. et al. Angiostatic effect of CXCR3 expressed on choroid neovascularization. Invest. Ophthalmol. Vis. Sci, 2012, vol. 53, p. 1999-2006.*

Ogilvie, P. et al. Eotaxin is a natural antagonist for CCR2 and an agonist for CCR5. Blood, 2001, vol. 97, p. 1920-1924.*

Damico, F.M. et al. New approaches and potential treatments for dry age-related macular degeneration. Arq. Bras. Oftalmol., 2012, vol. 75, No. 1, p. 71-75.*

(Continued)

*Primary Examiner* — Robert S Landsman
*Assistant Examiner* — Bruce D. Hissong

(57) ABSTRACT

The invention provides compositions and methods of predicting a subject's risk of developing age-related macular degeneration (AMD) and methods of treating, delaying, or preventing the development and progression of AMD.

6 Claims, 9 Drawing Sheets

Specification includes a Sequence Listing.

(56) References Cited

U.S. PATENT DOCUMENTS

| | | |
|---|---|---|
| 7,138,229 B2 | 11/2006 | Hu et al. |
| 7,183,413 B2 | 2/2007 | Lin et al. |
| 7,244,555 B2 | 7/2007 | Hu et al. |
| 7,332,294 B2 | 2/2008 | Kelvin et al. |
| 7,378,524 B2 | 5/2008 | Lin et al. |
| 7,405,275 B2 | 7/2008 | Qin et al. |
| 7,407,655 B2 | 8/2008 | Loetscher et al. |
| 7,427,487 B2 | 9/2008 | Villegas et al. |
| 7,541,435 B2 | 6/2009 | Proudfoot et al. |
| 7,622,264 B2 | 11/2009 | Fasano et al. |
| 2003/0119854 A1 | 6/2003 | Schell et al. |
| 2003/0158392 A1 | 8/2003 | Loetscher et al. |
| 2003/0166589 A1 | 9/2003 | Karin |
| 2004/0009503 A1 | 1/2004 | Fu et al. |
| 2004/0063779 A1 | 4/2004 | Dollinger et al. |
| 2004/0072237 A1 | 4/2004 | Schweitzer |
| 2004/0096446 A1 | 5/2004 | Lane |
| 2004/0141951 A1 | 7/2004 | Rothenberg et al. |
| 2004/0197303 A1 | 10/2004 | Merzouk et al. |
| 2004/0209902 A1 | 10/2004 | Lin et al. |
| 2005/0070573 A1 | 3/2005 | Lin et al. |
| 2005/0070582 A1 | 3/2005 | Li et al. |
| 2005/0090504 A1 | 4/2005 | Gong et al. |
| 2005/0112688 A1 | 5/2005 | Hu et al. |
| 2005/0113414 A1 | 5/2005 | Watson et al. |
| 2005/0153979 A1 | 7/2005 | Anderskewitz et al. |
| 2005/0176708 A1 | 8/2005 | Luckhurst et al. |
| 2005/0182094 A1 | 8/2005 | Sanganee et al. |
| 2005/0182095 A1 | 8/2005 | Ting et al. |
| 2005/0191293 A1 | 9/2005 | Deshpande et al. |
| 2005/0197325 A1 | 9/2005 | Batt et al. |
| 2005/0197373 A1 | 9/2005 | Batt et al. |
| 2005/0222118 A1 | 10/2005 | Le Grand et al. |
| 2005/0234034 A1 | 10/2005 | Pennell et al. |
| 2005/0250745 A1 | 11/2005 | Seddon |
| 2005/0272936 A1 | 12/2005 | Axten et al. |
| 2006/0036093 A1 | 2/2006 | Lin et al. |
| 2006/0040329 A1 | 2/2006 | Kelvin et al. |
| 2006/0063763 A1 | 3/2006 | Schall et al. |
| 2007/0048801 A1 | 3/2007 | Fasano et al. |
| 2007/0066523 A1 | 3/2007 | Merzouk et al. |
| 2007/0116669 A1 | 5/2007 | Merzouk et al. |
| 2007/0149557 A1 | 6/2007 | Collins et al. |
| 2007/0172446 A1 | 7/2007 | Blatt |
| 2007/0197589 A1 | 8/2007 | Watson et al. |
| 2008/0063646 A1 | 3/2008 | Balasa et al. |
| 2008/0312215 A1 | 12/2008 | Cole et al. |
| 2009/0030012 A1 | 1/2009 | Adams et al. |
| 2009/0030039 A1 | 1/2009 | Coesemans et al. |
| 2009/0131312 A1 | 5/2009 | Blatt et al. |
| 2009/0143413 A1 | 6/2009 | Adams et al. |
| 2009/0169561 A1 | 7/2009 | Fischer et al. |
| 2009/0208486 A1 | 8/2009 | Taketo et al. |
| 2009/0285835 A1 | 11/2009 | Qin et al. |

FOREIGN PATENT DOCUMENTS

| | | | |
|---|---|---|---|
| WO | WO 98/25605 A1 | 6/1998 |
| WO | WO 99/04794 A1 | 2/1999 |
| WO | WO 99/06085 A1 | 2/1999 |
| WO | WO 99/17773 A1 | 4/1999 |
| WO | WO 99/32100 A2 | 7/1999 |
| WO | WO 99/38514 A1 | 8/1999 |
| WO | WO 99/40913 A1 | 8/1999 |
| WO | WO 99/55324 A1 | 11/1999 |
| WO | WO 99/55330 A1 | 11/1999 |
| WO | WO 00/04003 A1 | 1/2000 |
| WO | WO 00/06146 A1 | 2/2000 |
| WO | WO 00/06153 A1 | 2/2000 |
| WO | WO 00/10965 A2 | 3/2000 |
| WO | WO 00/21916 A1 | 4/2000 |
| WO | WO 00/27800 A1 | 5/2000 |
| WO | WO 00/27835 A1 | 5/2000 |
| WO | WO 00/27843 A1 | 5/2000 |
| WO | WO 00/29377 A1 | 5/2000 |
| WO | WO 00/31032 A1 | 6/2000 |
| WO | WO 00/31033 A1 | 6/2000 |
| WO | WO 00/34278 A1 | 6/2000 |
| WO | WO 00/35449 A1 | 6/2000 |
| WO | WO 00/35451 A1 | 6/2000 |
| WO | WO 00/35452 A1 | 6/2000 |
| WO | WO 00/35453 A1 | 6/2000 |
| WO | WO 00/35454 A1 | 6/2000 |
| WO | WO 00/35876 A1 | 6/2000 |
| WO | WO 00/35877 A1 | 6/2000 |
| WO | WO 00/37455 A1 | 6/2000 |
| WO | WO 00/38680 A1 | 7/2000 |
| WO | WO 00/39125 A1 | 7/2000 |
| WO | WO 00/40239 A1 | 7/2000 |
| WO | WO 00/41685 A1 | 7/2000 |
| WO | WO 00/42045 A2 | 7/2000 |
| WO | WO 00/42852 A1 | 7/2000 |
| WO | WO 00/46195 A1 | 8/2000 |
| WO | WO 00/46196 A1 | 8/2000 |
| WO | WO 00/46197 A1 | 8/2000 |
| WO | WO 00/46198 A1 | 8/2000 |
| WO | WO 00/46199 A2 | 8/2000 |
| WO | WO 00/51607 A1 | 9/2000 |
| WO | WO 00/51608 A1 | 9/2000 |
| WO | WO 00/51609 A1 | 9/2000 |
| WO | WO 00/51610 A1 | 9/2000 |
| WO | WO 00/53172 A1 | 9/2000 |
| WO | WO 00/53175 A1 | 9/2000 |
| WO | WO 00/53600 A1 | 9/2000 |
| WO | WO 00/56729 A1 | 9/2000 |
| WO | WO 00/58305 A1 | 10/2000 |
| WO | WO 00/59497 A1 | 10/2000 |
| WO | WO 00/59498 A1 | 10/2000 |
| WO | WO 00/59502 A1 | 10/2000 |
| WO | WO 00/59503 A1 | 10/2000 |
| WO | WO 00/62814 A1 | 10/2000 |
| WO | WO 00/66112 A1 | 11/2000 |
| WO | WO 00/66141 A2 | 11/2000 |
| WO | WO 00/66551 A1 | 11/2000 |
| WO | WO 00/66558 A1 | 11/2000 |
| WO | WO 00/66559 A1 | 11/2000 |
| WO | WO 00/68203 A1 | 11/2000 |
| WO | WO 00/69432 A1 | 11/2000 |
| WO | WO 00/69815 A1 | 11/2000 |
| WO | WO 00/73327 A1 | 12/2000 |
| WO | WO 00/76933 A2 | 12/2000 |
| WO | WO 01/09088 A1 | 2/2001 |
| WO | WO 2009/067317 A2 | 5/2009 |

OTHER PUBLICATIONS

Scolletta, S. et al. Vitamin D receptor agonists target CXCL10: New therapeutic tools for resolution of inflammation. Mediators of Inflammation, 2013, vol. 2013, Article ID 876319, p. 1-11.*

Nowak JZ, "Age-related macular degeneration (AMD): pathogenesis and therapy", 2006 Pharmacol Rep, 58:353-363.

Zarbin MA, "Current Concepts in the Pathogenesis of Age-Related Macular Degeneration", 2004 Archives of ophthalmology, 122:598-614.

Ng EW and Adamis AP, "Targeting angiogenesis, the underlying disorder in neovascular age-related macular degeneration", 2005 Canadian Journal of Ophthalmology, 40:352-368.

Saint-Geniez M, et al., "An essential role for RPE-derived soluble VEGF in the maintenance of the choriocapillaris", 2009 Proceedings of the National Academy of Sciences of the USA, 106:18751-18756.

Boulday G et al., "Vascular Endothelial Growth Factor-Induced Signaling Pathways in Endothelial Cells That Mediate Overexpression of the Chemokine IFN-γ-Inducible Protein of 10 kDa in Vitor and In Vivo", 2006 J Immunol, 176:3098-3107.

Angiolillo AL et al., "Human Interferon-inducible Protein 10 is a Potent Inhibitor of Angiogenesis In Vivo", 1995 The Journal of experimental medicine, 182:155-162.

Tager AM et al., "Inhibition of Pulmonary Fibrosis by the Chemokine IP-10/CXCL10", 2004 American Journal of Respiratory Cell and Molecular Biology, 31:395-404.

(56) References Cited

OTHER PUBLICATIONS

Luster AD et al., "The IP-10 Chemokine Binds to a Specific Cell Surface Heparan Sulfate Site Shared with Platelet Factor 4 and Inhibits Endothelial Cell Proliferation", 1995 The Journal of Experimental Medicine, 182:219-231.
Campanella GS et al., "CXCR3 and Heparin Binding Sites of the Chemokine IP-10 (CXCL10)", 2003 The Journal of Biological Chemistry, 278:17066-17074.
Hale LP and Cianciolo G, "Treatment of experimental colitis in mice with LMP-420, an inhibitor of TNF transcription", 2008 Journal of Inflammation, 5:4.
Fryer et al., "Neuronal eotaxin and the effects of CCR3 antagonist on airway hyperreactivity and M2 receptor dysfunction", 2006 Journal of Clinical Investigation, 116:1.
Tang et al., "Early Enhanced Expression of Interferon-Inducible Protein-10 (CX CL-10) and Other Chemokines Predicts Adverse Outcome in Severe Acute Respiratory Syndrome", 2005 Clinical Chemistry 51:12, 2333-2340.
Kawamura et al., "CXCR3 Chemokine Receptor—Plasma IP10 Interaction in Patients With Coronary Artery Disease", 2003 Circulation Journal 67:851-854.
Rotondi et al., "High Pretransplant Serum Levels of CXCL10/IP-10 Are Related to Increased Risk of Renal Allograft Failure", 2004 American Journal of Transplantation 4:1466-1474.
Miles et al., "Age-related increases in circulating inflammatory markers in men are independent of BMI, blood pressure and blood lipid concentrations", 2008 Atherosclerosis 196:298-305.
Delori, F.C. et al., "Autofluorescence Distribution Associated with Drusen in Age-Related Macular Degeneration", 2000 Investigative Ophthalmology & Visual Science, 41:496-504.
Zhou J. et al., "Complement Activation by photooxidation products of A2E, a lipofuscin constituent of the retinal pigment epithelium", 2006 Proceedings of the National Academy of Sciences USA, 103:16182-16187.
Hollyfield J. G. et al., "Oxidative damage-induced inflammation initiates age-related macular degeneration", 2008 Nature medicine, 14:194-198.
Anderson D. H. et al., "A Role for Local Inflammation in the Formation of Drusen in the Aging Eye", 2002 American Journal of Ophthalmology, 134:411-431.
Russell S. R. et al., "Location, Substructure, and Composition of Basal Laminar Drusen Compared with Drusen Associated with Aging and Age-Related Macular Degeneration", 2000 American Journal of Ophthalmology, 129:205-214.
Crabb J. W. et al., "Drusen porteome analysis: An approach to the etiology of age-related macular degeneration", 2002 Proceedings of the National Academy of Sciences USA, 99:14682-14687.
Penfold P. L. et al., "Immunological and Aetiological Aspects of Macular Degeneration", 2001 Progress in retinal and eye research, 20:385-41.
Romagnani P. et al., "CXC chemokines: the regulatory link between inflammation and angiogenesis", 2004 Trends in immunology, 25:201-209.
Luster A.D., "Chemokines—Chemotactic Cytokines that Mediate Inflammation", 1998 The New England Journal of Medicine, 338:436-445.
Oh, H. et al., "The Potential Angiogenic Role of Macrophages in the Formation of Choroidal Neovascular Membranes", 1999 Investigative Ophthalmology & Visual Science, 40:1891-1898.
An E. et al., "Effect of TNF-alpha on human ARPE-19-secreted proteins", 2008 Molecular Vision, 14:2292-2303.
Salcedo R. et al., "Eotaxin (CCL11) Induces in Vivo Angiogenic Responses by Human CCR3+ Endothelial Cells", 2001 J. Immunol., 166:7571-7578.
Takeda A. et al., "CCR3 is a therapeutic and diagnostic target for neovascular age-related macular degeneration", 2009 Nature, 460:225-230.
Nakamura T. et al., "A Specific CCR3 Chemokine Receptor Antagonist Inhibits Both Early and Late Phase Allergic Inflammation in the Conjunctiva", Immunol. Res., 2006, 33:213-222.
Suzuki K., et al., "In vitro and in vivo characterization of a novel CCR3 antagonist, YM-344031", Biochem. Blophys. Res. Commun., 2006, 339:1217-1223.
Morokata T. et al., "A Novel, Selective, and Orally Available Antagonist for CC Chemokine Receptor 3", J. Pharmacol. Exp. Ther., 2006, 317:244-250.
Ting, P.C., et al., "The synthesis of substituted bipiperidine amide compounds as CCR3 ligands: Antagonists versus agonists", Biorg. Med. Chem. Lett., 2005, 15:3020-3023.
Beasley R., et al., "Prevalence and etiology of asthma", J. Allergy Clin. Immunol., 2000, 105:S466-S472.
Forbes I. T. et al., "CCR2B receptor antagonists: conversion of a weak HTS hit to a potent lead compound", Bioorg. Med. Chem. Lett., 2000, 10, 1803.

\* cited by examiner

Wet AMD results, with active Wet AMD patients undergoing Tx included in the Wet AMD column.

Wet AMD results, with active Wet AMD patients undergoing Tx included in the Wet AMD column.

Wet AMD results, with active Wet AMD patients undergoing Tx included in the Wet AMD column.

SEQUENCE LISTING

<160> NUMBER OF SEQ ID NOS: 2

<210> SEQ ID NO 1
<211> LENGTH: 98
<212> TYPE: PRT
<213> ORGANISM: human
<220> FEATURE:
<221> NAME/KEY: PEPTIDE
<222> LOCATION: (1)..(98)

<400> SEQUENCE: 1

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 2
<211> LENGTH: 99
<212> TYPE: PRT
<213> ORGANISM: human
<220> FEATURE:
<221> NAME/KEY: PEPTIDE
<222> LOCATION: (1)..(99)

<400> SEQUENCE: 2

Met Lys Val Ser Ala Ala Leu Leu Trp Leu Leu Val Ala Ala Ala
1               5                   10                  15

Phe Ser Pro Gln Gly Leu Thr Gly Pro Asp Ser Val Ala Thr Thr Cys
            20                  25                  30

Cys Phe Thr Leu Thr Asn Lys Lys Ile Pro Leu Gln Arg Leu Glu Ser
            35                  40                  45

Tyr Arg Arg Ile Ile Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Tyr Leu Asp Arg Lys Ser Pro Thr
                85                  90                  95

Pro Lys Pro

METHODS FOR TREATMENT OF AGE-RELATED MACULAR DEGENERATION

CROSS-REFERENCE TO RELATED APPLICATIONS

This application is a division of U.S. Ser. No. 13/283,739, filed Oct. 28, 2011 which is a continuation-in-part of PCT application number PCT/US2010/032801, filed Apr. 28, 2010, which claims the priority of U.S. provisional application No. 61/287,248, filed Dec. 17, 2009, and U.S. provisional application No. 61/173,257, filed Apr. 28, 2009, the respective disclosures of which are incorporated by reference herein in their entirety.

BACKGROUND OF THE INVENTION

Age-related macular degeneration (AMD) affects more than 10 million Americans, and is the leading cause of blindness for those aged fifty-five and older in the United States. AMD is caused by the deterioration of the central portion of the retina, the inside surface at the back of the eye. Although AMD can lead to vision loss, AMD typically has a preclinical, asymptomatic phase in which waste material accumulates in the space between Bruch's membrane and the epithelial layer, forming yellow-white spots known as drusen. As such, there is a need to develop techniques for early diagnosis and treatment of AMD to prevent or delay vision loss associated with the disease.

SUMMARY OF THE INVENTION

The present invention is based in part on the discovery of a relationship between certain biomarkers, e.g., IP-10 (interferon-gamma inducible protein-10; also known as C7) and Eotaxin, and the progression of age-related macular degeneration (AMD). Thus, in one aspect, the invention provides diagnostic methods that determine the levels of AMD biomarkers. This information is used to predict a subject's risk of developing AMD and/or progression to more advanced stages of AMD. The invention also provides methods of treating, preventing, and/or delaying the development or progression of AMD.

The invention provides a method of identifying a subject at risk of developing AMD comprising providing a test sample from a subject and measuring in the test sample the levels of IP-10. Subsequently, the levels of IP-10 in the test sample are compared to a reference level of IP-10, wherein a higher level of IP-10 in the test sample compared to the reference level of IP-10 is indicative of certain risk of AMD. Preferably, the age of the subject is also determined, and the reference level of IP-10 is obtained from one or more individuals that are age-mediated, e.g., within two years of age of the subject. Elevated serum levels of IP-10 in a patient fifty-five years of age or older, e.g., 56, 57, 58, 59, 60, 65, 70, 75, 80, 85, or 90 years of age or older indicates a high risk of developing AMD. Optionally, the medical history of the subject is also determined. The risk is assessed by analyzing the medical history of the subject, the age of the subject, and biological fluid levels, e.g., serum levels, of IP-10.

In one aspect, the diagnosis is an "early diagnosis", e.g., prior to the development of clinical signs or phenotype associated with AMD. Optionally, IP-10 levels are measured with an enzyme-linked immunosorbent assay (ELISA) or other immunohistochemical techniques known to those skilled in the art, e.g., multi-ELISA assays such as, but not limited to, Luminex® or Bio-plex® assays. The test sample is a biological fluid. Examples of biological fluids include whole blood, serum, plasma, spinal cord fluid, urine, tears and saliva. Preferably, the test sample is serum or urine.

In one aspect, the method further comprises measuring in the test sample the levels of eotaxin and comparing the levels of eotaxin in the test sample to a reference level of eotaxin, wherein a higher level of eotaxin in the test sample compared to the reference level of eotaxin is indicative of AMD.

The invention also provides a method of identifying a subject at risk of developing AMD comprising providing a test sample from a subject and measuring in the test sample the levels of eotaxin. The levels of eotaxin in the test sample are compared to a reference level of eotaxin, wherein a higher level of eotaxin in the test sample compared to the reference level of eotaxin is indicative of a certain risk of AMD. Preferably, the age of the subject is also determined, and the reference level of eotaxin is obtained from one or more individuals that are within two years of age of the subject. Elevated serum levels of eotaxin in a patient fifty-five years of age or older, e.g., 56, 57, 58, 59, 60, 65, 70, 75, 80, 85, or 90 years of age or older indicates a high risk of developing AMD. Optionally, the medical history of the subject is also determined. The risk is assessed by analyzing the medical history of the subject, the age of the subject, and the serum levels of Eotaxin.

In one aspect, the diagnosis is an "early diagnosis", e.g., prior to the development of clinical signs or phenotype associated with AMD. Optionally, the eotaxin levels are measured with an enzyme-linked immunosorbent assay (ELISA) or other immunohistochemical techniques known to those skilled in the art, e.g., multi-ELISA assays such as, but not limited to, Luminex® or Bio-plex® assays. The test sample is a biological fluid. Examples of biological fluids include whole blood, serum, plasma, spinal cord fluid, urine, tears and saliva. Preferably, the test sample is serum or urine.

Also provided are methods of treating AMD in a subject comprising administering to the subject a composition that inhibits the activity of IP-10. For example, IP-10 activity is inhibited by 10%, 20%, 50%, 75% or by 2 fold, 5 fold, or 20 fold or more. Activities of IP-10 include binding of IP-10 to its receptor, CXCR3. A reduction in the activity of IP-10 is measured by, e.g., detecting a reduction in the level of binding of IP-10 to its receptor, CXCR3. Other activities of IP-10 include chemotactic activity. A reduction in the activity of IP-10 is measured by, e.g., detecting a reduction in the level of chemotaxis. In one aspect, the AMD is dry AMD. In another aspect, the AMD is wet AMD. A method for inhibiting an activity of IP-10 is carried out by administering a composition comprising a polynucleotide, a polypeptide, an antibody, a compound, or a small molecule that inhibits the transcription, transcript stability, translation, modification, localization, secretion, or function of a polynucleotide or polypeptide encoding IP-10. In one aspect, the composition that inhibits the activity of IP-10 is a neutralizing antibody, a solubilized receptor that binds circulating IP-10 or a CXCR3 receptor antagonist. Suitable CXCR3 receptor antagonists include, but are not limited to antibodies, peptides or small molecules. In one aspect, the composition that inhibits the activity of IP-10 is a CXCRR3 receptor antagonist selected from the group consisting of NBI-74330, NSC651016, LMP420, AZD3778, T0906487, AMG487, TAK779, and NBI-74330. Optionally, the composition that inhibits the activity of IP-10 comprises a non-selective cytokine inhibitor that has cross-reactivity (cross-over inhibitor activity) against IP-10 or eotaxin receptors.

The composition is administered topically, locally, intravitreally, orally, subcutaneously, intravenously, intraocularly, or peribulbarly. Preferably, the composition is administered locally. Optionally, the method further comprises administering to the subject a composition that inhibits the activity of eotaxin.

Also described are methods of treating AMD in a subject comprising administering to the subject a composition that inhibits the activity of eotaxin. For example, eotaxin activity is inhibited by 10%, 20%, 50%, 75% or by 2 fold, 5 fold, or 20 fold or more. Activities of eotaxin include binding of eotaxin to a chemokine receptor, such as a G-protein-coupled receptor, e.g., a CC Chemokine receptor, e.g., CCR2, CCR3, or CCR5. A reduction in the activity of eotaxin is measured by, e.g., detecting a reduction in the level of binging of eotaxin to its receptor. Other activities of eotaxin include chemotactic activity. A reduction in the activity of eotaxin is measured by, e.g., detecting a reduction in the level of chemotaxis. In one aspect, the AMD is dry AMD. In another aspect, the AMD is wet AMD. A method for inhibiting an activity of eotaxin is carried out by administering a composition comprising a polynucleotide, a polypeptide, an antibody, a compound, or a small molecule that inhibits the transcription, transcript stability, translation, modification, localization, secretion, or function of a polynucleotide or polypeptide encoding eotaxin. Preferably, the composition that inhibits the activity of eotaxin is a neutralizing antibody, a solubilized receptor that binds circulating eotaxin, or a CC receptor antagonist. Suitable CC receptor antagonists include, but are not limited to antibodies, peptides or small molecules. In one aspect, the composition that inhibits the activity of eotaxin is a CCR3 receptor antagonist selected from the group consisting of DPC168, BMS570520, Ki19003, SB328437, GW701897, YM-344031 and GW766994. Optionally, the composition that inhibits the activity of eotaxin comprises a non-selective cytokine inhibitor that has cross-reactivity (cross-over inhibitor activity) against IP-10 or eotaxin receptors.

The composition is administered topically, locally, intravitreally, orally, subcutaneously, intravenously, intraocularly, or peribulbarly. Preferably the administration is performed locally. The AMD is dry AMD or wet AMD.

The invention also provides a method of preventing AMD in a subject at risk thereof comprising administering to the subject a composition that inhibits the activity of IP-10 or a composition that inhibits the activity of eotaxin.

The composition that inhibits the activity of IP-10 or eotaxin or both IP-10 and eotaxin is administered topically, intravitreally, orally, subcutaneously, intravenously, intraocularly, or peribulbarly. Preferably the administration is performed locally. Alternatively, the composition is administered topically as eye drops, ointment, gel, paste, liquid, aerosol, mist, polymer, film, emulsion, or suspension. In one aspect, the composition is incorporated into or coated onto a contact lens, from which one or more molecules diffuse away from the lens or are released in a temporally-controlled manner. Alternatively, the composition is released to the eye by a slow-releasing device either topically or intravitreously.

Administering the formulation to the eye can involve implantable devices, depending on the precise nature of the formulation and the desired outcome of the administration. Specifically, a composition of the invention is delivered directly to the eye, (e.g., slow release devices such as pharmaceutical drug delivery sponges implanted in the cul-de-sac or implanted adjacent to the sclera or within the eye), using techniques well known by those of ordinary skill in the art. It is further contemplated that a polypeptide as disclosed herein is formulated in intraocular inserts or implantable devices as described further below.

The ophthalmic formulations of the invention are administered in any form suitable for ocular drug administration, e.g., dosage forms suitable for topical administration, a solution or suspension for administration as eye drops or eye washes, ointment, gel, liposomal dispersion, colloidal microparticle suspension, or the like, or in an ocular insert, e.g., in an optionally biodegradable controlled release polymeric matrix. The ocular insert is implanted in the conjunctiva, sclera, pars plana, anterior segment, or posterior segment of the eye. Implants provide for controlled release of the formulation to the ocular surface, typically sustained release over an extended time period. Additionally, in a preferred embodiment, the formulation is entirely composed of components that are naturally occurring and/or as GRAS ("Generally Regarded as Safe") by the U.S. Food and Drug Administration.

The isolated polypeptides are purified or synthetic. By "purified" or "substantially purified" is meant an IP-10 polypeptide, an eotaxin polypeptide, or biologically active portion thereof that is substantially free of cellular material or other contaminating macromolecules, e.g., polysaccharides, nucleic acids, or proteins, from the cell or tissue source from which the polypeptide is derived. The phrase "substantially purified" also includes an IP-10 polypeptide or an eotaxin polypeptide that is substantially free from chemical precursors or other chemicals when chemically synthesized. The language "substantially free of cellular material" includes preparations of an IP-10 polypeptide or an eotaxin polypeptide that are separated from cellular components of the cells from which they are isolated.

Also provided are methods of monitoring treatment of AMD comprising providing a test sample from a subject and measuring in the test sample the levels of IP-10. A composition that inhibits the activity of IP-10 is administered to a subject. After administration, e.g., about 1 hour, about 2 hours, about 6 hours, about 12 hours, about 24 hours, about 7 days, about 1 month; about 6 months; about 12 months, or about 1 year after administration, a second test sample from a subject is provided. The levels of IP-10 in said second sample are measured. The levels of IP-10 in the second test sample are compared to the levels of IP-10 in the first test sample, wherein a higher level of IP-10 in the first test sample compared to the second sample indicates the treatment is effective.

In one aspect, the risk for a patient to develop AMD can be read on a graphical calculating device, e.g., a nomogram. The nomogram includes a plurality of numerical relations or parameters such as, but not limited to, age, levels of eotaxin and IP-10 obtained from a bodily sample, genetic factors, and inflammatory systemic diseases, to evaluate the risk level of developing AMD as very low (<5%), low (5-25%), low moderate (25-49%), moderate (50-74%), high (75-90%) or very high (>90%).

Also described are kits for identifying a subject at risk of developing AMD. The kits comprise a first reagent that detects IP-10; a second reagent that detects eotaxin; and directions for using the kit. Specifically, the invention provides a kit for measuring the levels of IP-10 and eotaxin in a patient to diagnose or prognosticate any form of AMD and early drusen formation. The kit is suitable for in-office testing of a bodily fluid of the patient. The kit includes a package of one or more assays for an AMD biomarker, and instructions for use in a method described herein, and optionally related materials such as marker level or range information for correlating the level of the marker as determined by the assay with a risk of development or progression of AMD.

The invention provides a device comprising (1) a recording module that records the IP-10 and eotaxin levels of a patient as well as the age of the patient and medical history of the patient; (2) a comparison module that compares the levels of IP-10 and eotaxin of the patient to the average levels of the population at the age of the patient; (3) a reading module that provides the risk of the patient to develop AMD.

Optionally, the predictive value of the biomarkers described herein for risk of development or progression of AMD is additive to other risk factors (e.g., smoking, obesity, body mass index, antioxidant intake, age, gender, family history of AMD, and history of systemic inflammatory diseases such as chronic infections or collagen vascular disease). Alternatively, the risk assessed with the biomarkers of the invention is independent of other risk factors.

The invention also provides a nomogram correlating the levels of IP-10 and eotaxin in a bodily fluid to the risk of developing AMD.

As used herein, "age-related macular degeneration" or "AMD" includes early, intermediate, and advanced AMD. "Advanced AMD" includes both dry AMD such as geographic atrophy and wet AMD.

As used herein "subject" or "patient" is a mammal, preferably a human.

As used herein "eotaxin" means any form of eotaxin (eotaxin-1, -2, -3 and others), but preferably "eotaxin-1".

The term "elevated levels" means serum levels higher than the average serum level for the population without AMD at a given age.

"High risk" means a risk higher than the average risk of the population at a given age.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

DETAILED DESCRIPTION OF THE INVENTION

Figure 1:
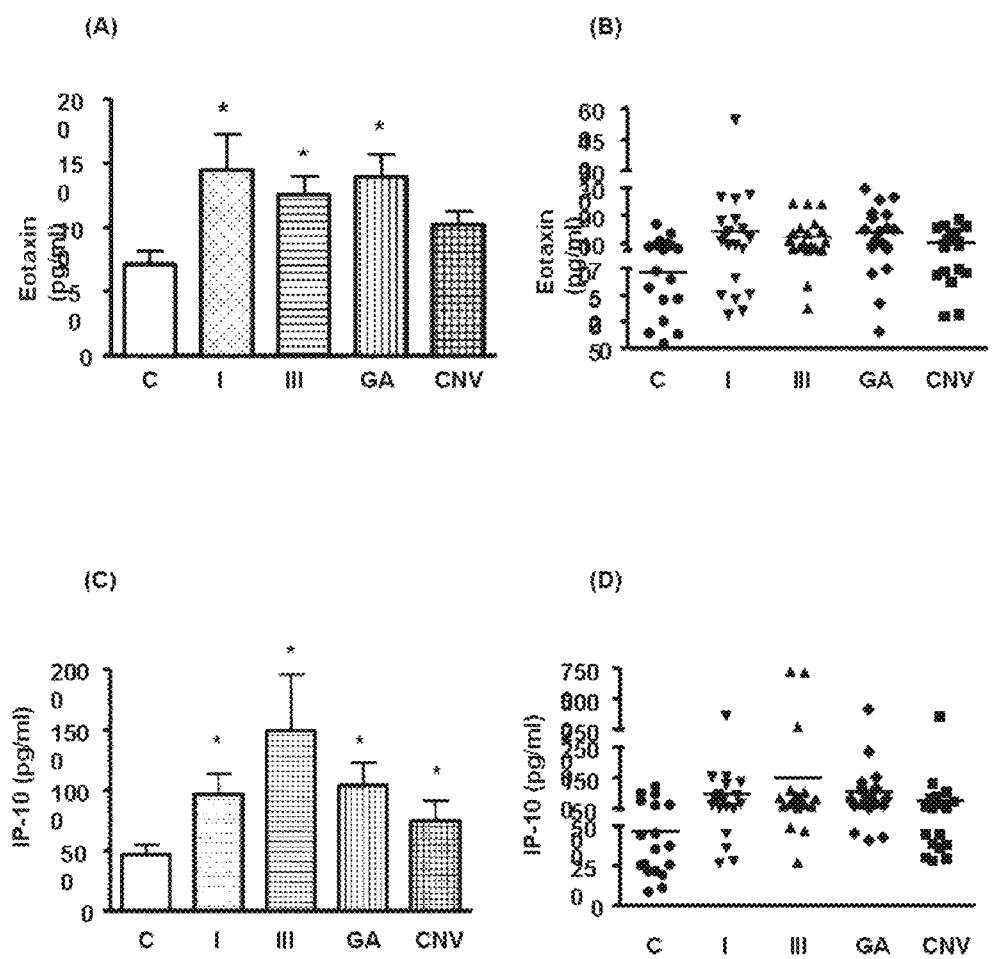
FIGS. 1A and 1B are bar graphs depicting the eotaxin levels for patients of the five following groups: C: control subject—no phenotypic evidence of AMD; I—AREDS 1, minimal drusen; III—AREDS 3, confluent drusen representing intermediate (dry) age-related maculopathy; GA—geographic atrophy—localized areas of retinal degeneration representing advanced dry AMD; CNV—choroidal neovascularization—development of vascularized collagen based scar tissue within the choroid as sign of wet AMD.
FIGS. 1C and D are bar graphs depicting the IP-10 levels for patients of the five following groups: C: control subject—no phenotypic evidence of AMD; I—Age-Related Eye Disease Study (AREDS) 1, minimal drusen; III—AREDS 3, confluent drusen representing intermediate (dry) age-related maculopathy; GA geographic atrophy—localized areas of retinal degeneration representing advanced dry AMD; CNV—choroidal neovascularization-development of vascularized collagen based scar tissue within the choroids as sign of wet AMD.

Age-related macular degeneration (AMD) is a medical condition usually of older adults resulting in loss of vision in the center of the visual field (the macula) because of damage to the retina. AMD occurs in "dry" and "wet" forms, and is a major cause of blindness in the elderly (>50 years). In the advanced stages, AMD can make it difficult or impossible to read or recognize faces, although enough peripheral vision remains unaffected to allow other activities of daily life. The inner layer of the eye is the retina, which contains nerves that communicate sight. Behind the retina is the choroid, which contains the blood supply to the retina. There are two forms of AMD: dry and wet. The "dry" form of AMD (most common), results from atrophy of the retinal pigment epithelial layer below the retina, which causes vision loss through loss of photoreceptors (rods and cones) in the central part of the eye. In the dry form, cellular debris called "drusen" accumulate between the retina and the choroid, leading to retinal degeneration. While no treatment is available for this condition, vitamin supplements with high doses of antioxidants, lutein and zeaxanthin, have been suggested by the National Eye Institute and others to slow the progression of dry macular degeneration and, in some patients, improve visual acuity. As such, there is a need for new therapies to treat "dry" AMD.

In the wet (exudative) form, which is more severe, blood vessels grow outward from the choroid behind the retina, leading to retinal degeneration. Specifically, neovascular or exudative AMD, the "wet" form of advanced AMD, causes vision loss due to abnormal blood vessel growth (choroidal neovascularization) in the choriocapillaris, through Bruch's membrane, ultimately leading to blood and protein leakage below the macula. Wet AMD is typically treated with laser coagulation, photodynamic therapy, and with medications that stop and sometimes reverse the growth of blood vessels, or in combination. Bleeding, leaking, and scarring from the membrane and its blood vessels eventually cause irreversible damage to the photoreceptors and rapid vision loss if left untreated. Until recently, no effective treatments were known for wet macular degeneration. However, new drugs, called anti-angiogenics or anti-VEGF (anti-Vascular Endothelial Growth Factor) agents, can cause regression of the abnormal blood vessels and improvement of vision when injected directly into the vitreous humor of the eye. The injections can be painful and frequently have to be repeated on a monthly or bi-monthly basis. Examples of these agents include ranibizumab (trade name Lucentis®), bevacizumab (trade name Avastin®, a close chemical relative of ranibizumab) and pegaptanib (trade name Macugen®). Photodynamic therapy has also been used to treat wet AMD. While therapies for "wet" AMD are available, there is a need for better therapies such as therapies requiring fewer intraocular injections and adjuvant therapies that would inhibit retinal neovascularization using pathways other than the VEGF pathway.

Therapeutic efforts aimed at halting the growth of the neovascular membrane in wet AMD include angiogenesis inhibitors, laser photocoagulation and photodynamic therapy. As new therapies for AMD are introduced, especially for dry AMD, early diagnosis of AMD prior to any visible phenotypic changes in the eye and identification of population that is at increased risk for developing AMD become more important.

AMD is a chronic disease that develops over decades and may lead to severely damaged vision (Zarbin M A, 2004 Archives of ophthalmology, 122:598-614). This process is initially heralded by accumulation in the aging retinal pigment epithelial (RPE) cells of lipofuscin granules from long-term turnover and recycling of photoreceptor outer segments (Delori F C et al., 2000 Investigative Ophthalmology & Visual Science, 41:496-504) and induction of oxidative stress (Nowak J Z, 2006 Pharmacol Rep, 58:353-363; Zhou J et al., 2006 Proceedings of the National Academy of Sciences USA, 103:16182-16187; Hollyfield J G, et al., 2008 Nature medicine, 14:194-198). Early phenotypic findings in AMD include the appearance of hard and soft drusen (Anderson D H et al., 2002 American Journal of Ophthalmology, 134:411-431). Some drusen constituents identified in proteomic studies include pro-inflammatory stimuli (Zhou J et al., 2006 Proceedings of the National Academy of Sciences USA, 103:16182-16187; Russell et al., 2000 American Journal of Ophthalmology, 129:205-214; Crabb et al., 2002 Proceedings of the National Academy of Sciences USA, 99:14682-14687).

It is currently accepted that inflammation plays an important role in the pathogenic progression of AMD (Zarbin M A, 2004 Archives of ophthalmology, 122:598-614; Hollyfield J G, et al., 2008 Nature medicine, 14:194-198; Penfold P L et al., 2001 Progress in retinal and eye research, 20:385-414). Thus, control of chronic inflammation may retard the progression to the advanced form of AMD and may limit visual loss from this disease. Chronic inflammation consists of a series of biological responses to harmful stimuli that include activation of subsets of immune cells, which are recruited to inflamed areas, angiogenesis and scar formation (Romagnani P et al., 2004 Trends in immunology, 25:201-209; Luster A D, 1998 The New England Journal of Medicine, 338:436-445). Inflammatory cells are regulated by a multitude of cytokines and inhibition of cytokine release may affect the disease outcome. Some cytokines have been implicated in AMD, including vascular endothelial growth factor (VEGF) which supports choroidal neovascularization (Ng E W and Adamis A P, 2005 Canadian Journal of Ophthalmology, 40:352-368). Interleukin 1-beta (IL-1β) and tissue necrosis factor-alpha (TNF-α) are also detected in AMD tissues (Oh H et al., 1999 Investigative Ophthalmology & Visual Science, 40:1891-1898; An E, et al., 2008 Molecular Vision, 14:2292-2303).

Markers of systemic inflammation such as c-reactive protein (CRP), IL-6, tumor necrosis factor alpha receptor II (TNF-R2), intracellular adhesion molecule (ICAM), lipid biomarkers, e.g., apolipoprotein and lipoprotein, and homocysteine have been reported to be predictive of development and progression of AMD (US 2005/0250745 A1). Elevated levels of these markers in otherwise healthy subjects are reportedly predictive of development and progression of AMD.

10 kDa interferon-gamma-induced protein (IP-10) also known as Chemokine (C—X—C motif) ligand 10 (CXCL10) is a small cytokine belonging to the CXC chemokine family. IP-10 is secreted by several cell types in response to IFN-γ. These cell types include monocytes, endothelial cells and fibroblasts. IP-10 has been attributed to several roles, such as chemoattraction for monocytes/macrophages, T cells, NK cells, and dendritic cells, promotion of T cell adhesion to endothelial cells, antitumor activity, and inhibition of bone marrow colony formation and angiogenesis. The gene for IP-10 is located on human chromosome 4 in a cluster among several other CXC chemokines. The sequence of IP-10 is as follows: mnqtailicc lifltlsgiq gvplsrt-vrc tcisisnqpv nprsleklei ipasqfcprv eiiatmkkkg ekrclnpesk aiknllkavs kerskrsp (SEQ ID NO: 1).

Eotaxin-1 also known as Chemokine (C—C motif) ligand 11 (CCL11) is a small cytokine belonging to the CC chemokine family. Eotaxin-1 selectively recruits eosinophils by inducing their chemotaxis, and therefore, is implicated in allergic responses. The effects of eotaxin-1 are mediated by its binding to a G-protein-coupled receptor known as a chemokine receptor. The gene for human CCL11 (scya11) is encoded on three exons and is located on chromosome 17. The sequence of Eotaxin-1 is as follows: mkvsaallwl llvaaafspq gltgpdsvat tccftltnkk iplqrlesyr riisgkcpqk avifk-tklak dicadpkkkw vqdsmkyldr ksptpkp (SEQ ID NO: 2).

Chemokine receptor CXCR3 is a G-protein-coupled receptor in the CC chemokine receptor family. Other names for CXCR3 are G protein-coupled receptor 9 (GPR9) and CD183. There are two variants of CXCR3: CXCR3-A binds to the CC chemokines CCL9 (MIG), CCL10, and CCL11 (IP-10, I-TAC) whereas CXCR3-B can also bind to CCL4 in addition to CCL9, CCL10, and CCL11. CXCR3 is expressed primarily on activated T lymphocytes and NK cells, and some epithelial cells and some endothelial cells. CXCR3 and CXCR5 are preferentially expressed on Th1 cells, whereas Th2 cells favor the expression of CXCR3 and CXCR4. CXCR3 ligands that attract Th1 cells can concomitantly block the migration of Th2 cells in response to CXCR3 ligands, thus enhancing the polarization of effector T cell recruitment.

CXCR3 has been implicated in the following diseases, atherosclerosis, multiple sclerosis, pulmonary fibrosis, type 1 diabetes, autoimmune myasthenia gravis, nephrotoxic nephritis, acute cardiac allograft rejection and possibly Celiac disease.

CC chemokine receptors are integral membrane proteins that specifically bind and respond to cytokines of the CC chemokine family. They represent one subfamily of chemokine receptors, a large family of G protein-linked receptors that are known as seven transmembrane (7-TM) proteins since they span the cell membrane seven times. To date, ten true members of the CC chemokine receptor subfamily have been described. These are named CCR1 to CCR10 according to the IUIS/WHO Subcommittee on Chemokine Nomenclature. The effects of eotaxin (CCL11) are mediated by its binding to a G-protein-linked receptor known as a chemokine receptor. Chemokine receptors for which CCL11 is a ligand include CCR2, CCR3 and CCR5.

The angiogenic characteristic of eotaxin was first proposed in 2001 (Salcedo R et al., 2001 J Immunol; 166:7571-7578). Inhibitors of the CCR3 receptor, or its ligands eotaxin (CCL11), eotaxin-2 (CCL24) or eotaxin-3 (CCL-26) have been proposed to inhibit ocular angiogenesis (U.S. patent application Ser. No. 12/247,772) and CCR3 blockade is claimed to be more effective than VEGF-A blockade at reducing choroidal neovascularization in the "wet" form of AMD (Takeda A et al., 2009 Nature, 460:225-230), but have not been identified as potential treatments for the "dry" form of AMD. Eotaxin was reported to be expressed in surgically-excised choroidal neovascular tissue as was its receptor CCR3.

As described herein, the systemic cytokine profile of subjects with AMD at different stages of the diseases were studied together with the expression of salient cytokines in postmortem eyes with AMD. The results of this study show that serum IP-10 and eotaxin are significantly elevated in subjects with AMD. It is particularly interesting that both cytokines are increased in the early stage of the disease. As described below, both IP-10 and eotaxin, alone or in combination are potential biomarkers for early detection of AMD prior to development of any significant phenotypic characteristics. As described herein, increased serum IP-10 concentrations matched its expression pattern in the eye, with respect to progression from early to intermediate stage AMD.

As described in more detail below, in the early stage of AMD, IP-10 serum levels were increased significantly (FIG. 1). Histological sections of eyes with early AMD exhibited increased immunoreactivity for IP-10 in the RPE (FIG. 3D) and some eyes had focal staining within the basal linear/laminar deposit. The peak serum IP-10 concentration was detected at the AREDS stage 3, remained high in GA, and decreased slightly in the subjects with CNV (P<0.03) when compared to the peak level. The immunoreactivity of IP-10 in the macular RPE of control eyes was absent or present focally and usually with a low staining intensity (FIG. 3B, Table 4). In eyes with early AMD, GA, and CNV, there was increased expression of IP-10 in RPE cells. Eyes with GA and CNV had loss of RPE in the center of the lesions, but residual RPE cells expressed IP-10 with more intense staining than that in control eyes.

RPE cells play a critical role in the blood-retinal barrier and in the maintenance of the photoreceptor. As RPE cells age or are subjected to oxidative stress, their expression profile of cytokines is altered and they may upregulate pro-inflammatory or pro-angiogenic cytokines such as VEGF, basic fibroblast growth factor-2, and interleukin 8 for wound healing or other pathological functions. The ability of IP-10 to antagonize the angiogenic effect of VEGF may be particularly important for the pathogenesis of CNV. RPE-derived soluble VEGF is essential in the maintenance of the choriocapillaris (Saint-Geniez M, et al., 2009 Proceedings of the National Academy of Sciences of the USA, 106:18751-18756). In-vitro and in-vivo studies show that VEGF can induce overexpression of IP-10 in endothelial cells (Boulday G et al., 2006 J Immunol, 176:3098-3107), but whether or not this may occur within the RPE is unknown. Endothelial cells within the CNV membrane and the connective tissue matrix associated with the CNV had strong expression of IP-10 (FIG. 3H), which is intriguing since IP-10 is well-known for its angiostatic and anti-fibrotic activities (Angiolillo A L et al., 1995 The Journal of experimental medicine, 182:155-162; Tager A M et al., 2004 American Journal of Respiratory Cell and Molecular Biology, 31:395-404). IP-10 inhibits endothelial cell proliferation by competing with endothelial cells for the binding sites of heparan sulfate proteoglycans resulting in attenuation of new vessel formation (Luster A D et al., 1995 The Journal of Experimental Medicine, 182:219-231; Campanella G S et al., 2003 The Journal of Biological Chemistry, 278:17066-17074). As described herein, the IP-10 observed within the CNV membrane may account for an important mechanism for dampening the effects of angiogenic and fibrotic cytokines released during development of CNV.

Figure 3:
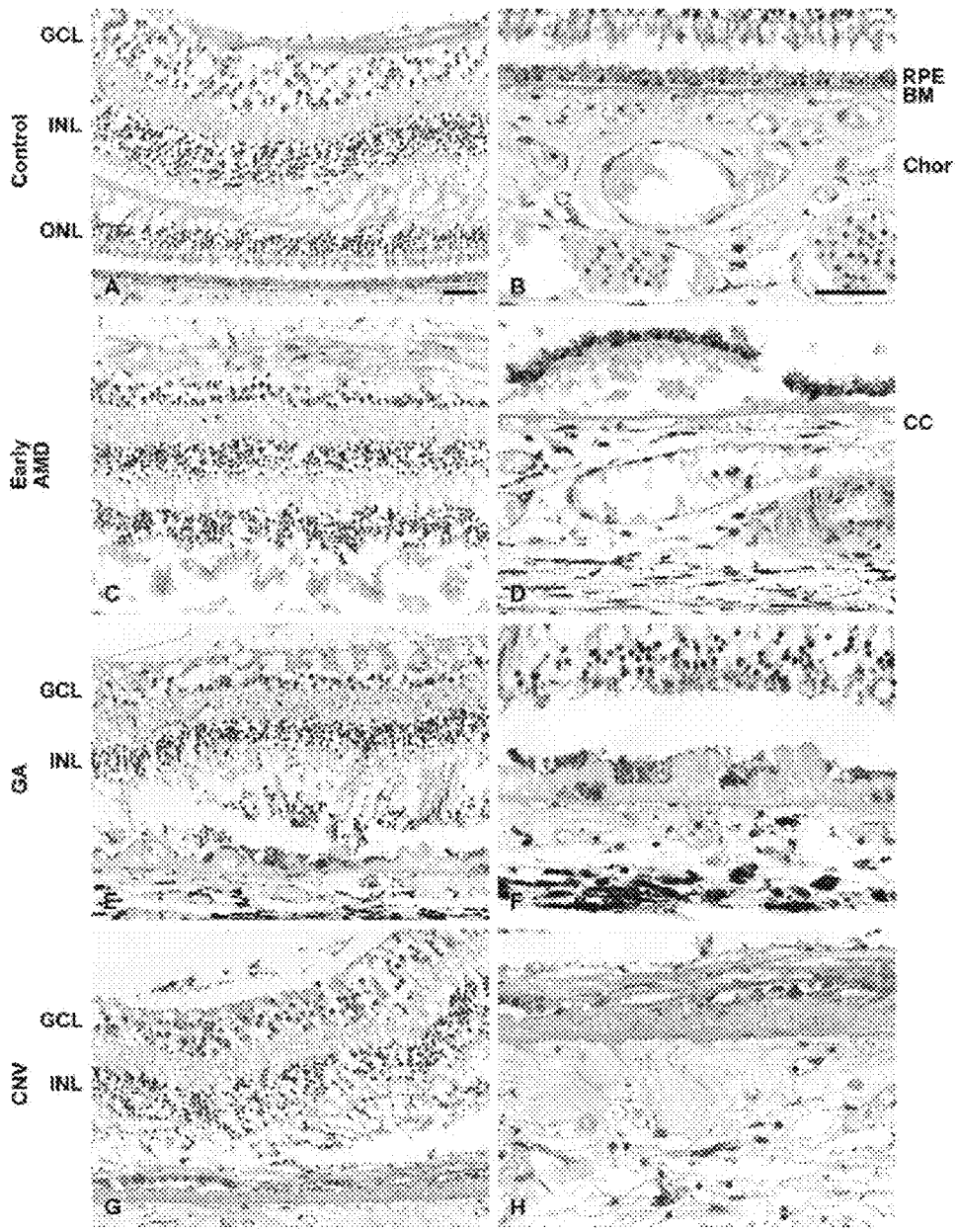
FIG. 3 is a series of photomicrographs depicting immunohistochemical localization of interferon gamma-inducible protein-10 (IP-10) in postmortem eyes with various stages of age-related macular degeneration (AMD) and in age-matched controls without AMD (A and B). IP-10 was detected using an alkaline phosphatase reagent; tissue was counterstained with hematoxylin and the nuclei are shown. IP-10 was expressed in the neurosensory retina in the nerve fiber layer, ganglion cell layer (GCL), inner nuclear layer (INL), outer nuclear layer (ONL), and photoreceptor outer segments; there was no consistent difference in staining among the eyes without (A and B) or with AMD (C, E, and G). There was enhanced expression of IP-10 in the RPE of eyes with early AMD (D), GA (F), and CNV (H). IP-10 accumulated focally within the layer of basal linear/laminar deposit in GA (F) and CNV (H), and it was uniformly and strongly expressed by neovascular endothelial cells and within the connective tissue matrix associated with the CNV (H). The magnification bars=50 µm.
Figure 4:
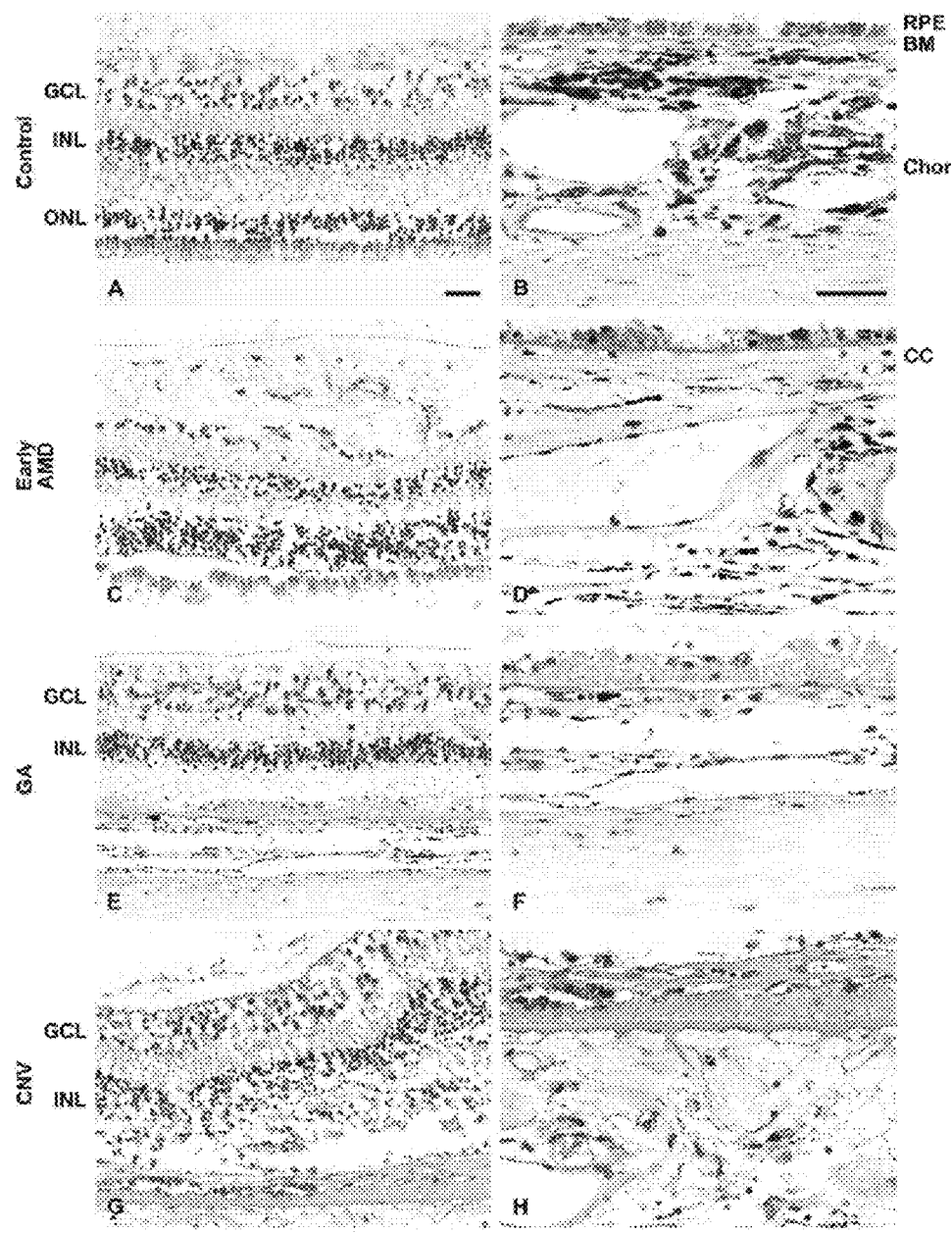
FIG. 4 is a series of photomicrographs depicting immunohistochemical localization of eotaxin in postmortem eyes with various stages of age-related macular degeneration (AMD) and in age-matched controls without AMD (A and B). Eotaxin was detected using an alkaline phosphatase reagent (Vector Red); tissue was counterstained with hematoxylin and the nuclei are shown. Eotaxin was expressed in the neurosensory retina in the nerve fiber layer, ganglion cell layer (GCL), inner nuclear layer (INL), outer nuclear layer (ONL), and photoreceptor outer segments; there was no consistent difference in staining among the eyes without (A and B) or with AMD (C, E, and G). There was enhanced expression of eotaxin in the RPE of eyes with early AMD (D), GA (F), and CNV (H). Eotaxin accumulated within the basal linear/laminar deposit in all stages of AMD, though the staining was often patchy (focal). Eotaxin was expressed by neovascular endothelial cells and it was often present within the connective tissue matrix associated with CNV (H). The magnification bars=50 µm.
Figure 5:
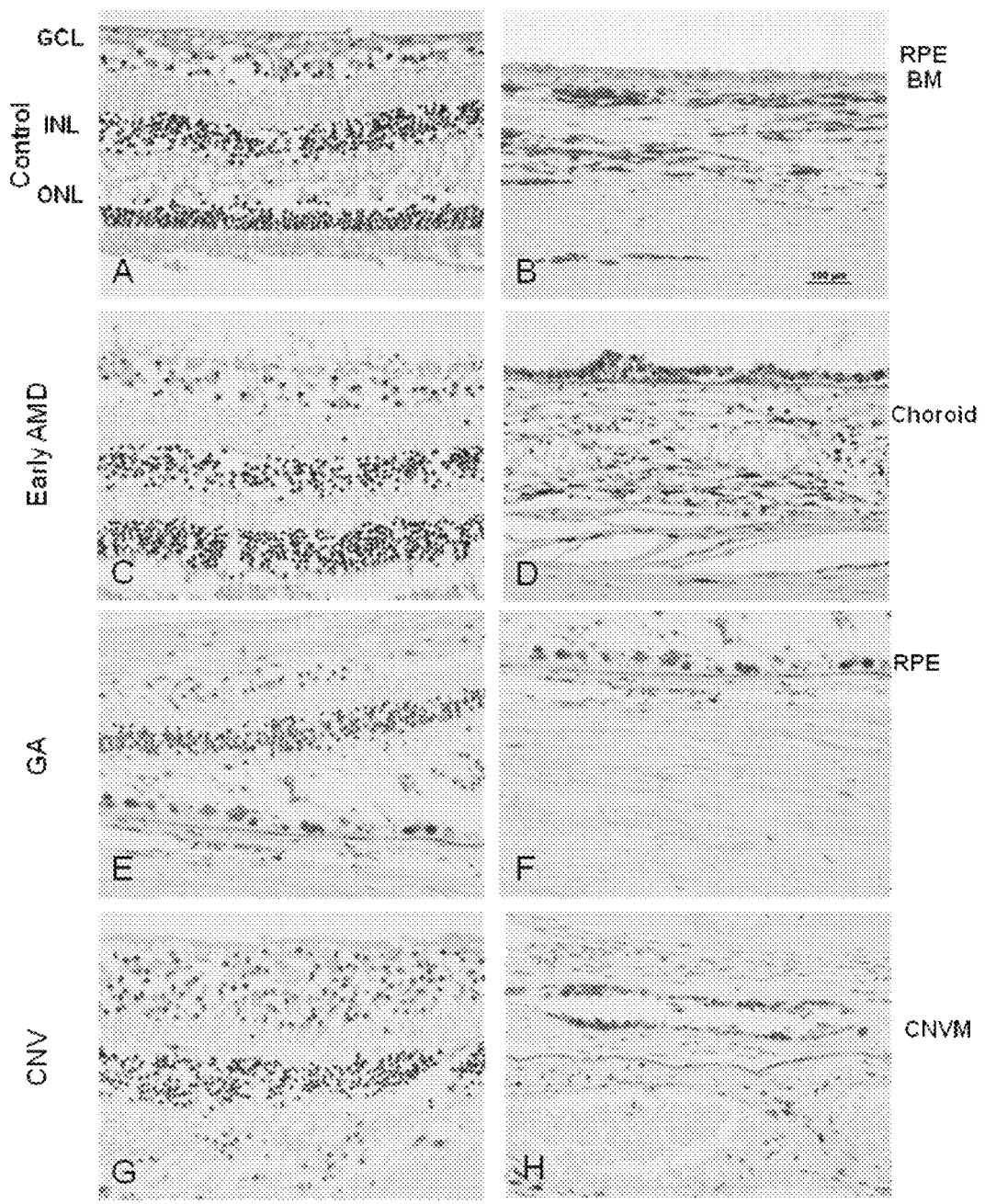
FIG. 5 is a series of photomicrographs depicting immunohistochemical localization of C—C chemokine receptor type 3 (CCR3) in postmortem human eyes with various stages of age-related macular degeneration (AMD) and in age-matched controls without AMD. Slides were deparaffinized, rehydrated and subjected to immunohistochemistry for expression of CCR3 receptor using alkaline phosphatase method and resolved with Vulcan Red stain. TOP panel: representative eye of a control subject (A and B) with no AMD shows trace expression of CCR3 within some choroidal spindle cells. Early AMD Panel (C and D): CCR3 expression is detected within RPE cells (arrow) and drusen (arrows) in eyes with dry AMD. GA Panel (E and F): Increased CCR3 expression is present in the inner nuclear layer (INL; left) as well as in the RPE and choriocapillaris (cc). CNV panel (G and H): CCR3 expression is detected in some retinal ganglion (RGC) cells, INL, and in endothelial cells associated with choroidal neovascular membrane (CNVM).

The expression of IP-10 and Eotaxin was examined in autopsy eyes of patients with different stages of AMD. Both IP-10 and eotaxin were expressed in the neurosensory retina in the nerve fiber layer, ganglion cell layer (GCL), inner nuclear layer (INL), outer nuclear layer (ONL), and photoreceptor outer segments (POS). As shown in FIG. 3, there was enhanced expression of IP-10 in the RPE of eyes with early AMD, GA, and CNV. IP-10 accumulated focally within the layer of basal linear/laminar deposit in GA and CNV, and it was uniformly and strongly expressed by neovascular endothelial cells and within the connective tissue matrix associated with the CNV. FIG. 4 illustrates enhanced expression of eotaxin in the RPE of eyes with early AMD, GA, and CNV. There was accumulation of eotaxin within the basal linear/laminar deposit in all stages of AMD, though the staining was patchy (focal) and less than that observed for IP-10. Similar to results for IP-10, eotaxin expression by neovascular endothelial cells was observed. FIG. 5 illustrates enhanced expression of CCR3 in the RPE of eyes with early AMD, GA, and CNV. CCR3 expression is detected in some retinal ganglion (RGC) cells, INL, and in endothelial cells associated with choroidal neovascular membrane (CNVM).

Enhanced expression of eotaxin and IP-10 in AMD patients at all stages of the disease demonstrates that both cytokines play a role in the pathogenesis of this disease.

IP-10 and eotaxin are targets to treat the "dry", as well as "wet" forms of AMD. Inhibiting the expression of IP-10 and eotaxin in the eye represents a novel therapeutic approach to treat dry and wet AMD. The identification of new targets for the treatment of "dry" AMD is particularly significant since no treatment is currently available.

Any compound which inhibits the activity of any eotaxin (including eotaxin-1, eotaxin-2 and eotaxin-3) is used in the present invention.

Suitable compounds to inhibit the activity of eotaxin and/or IP-10 are described in Table 6. Suitable compounds include those that do not directly inhibit IP-10 and/or eotaxin, but exhibit cross-reactivity with IP-10 and/or eotaxin.

In one aspect, LMP-420 (2-amino-6-chloro-9[5(dihydroxyborylpentyl]-purine); available from Scynexis, Inc.), an anti-inflammatory analogue that is a potent inhibitor of tumor necrosis factor-α (TNF-α) and monocyte chemotactic protein-1 (MCP-1), also inhibits IP-10 and/or eotaxin due to cross-reactivity. Specifically, LMP-420 is a boronic acid-containing purine nucleoside analogue that transcriptionally inhibits TNF production, but is non-toxic to TNF-producing cells (Hale L P and Cianciolo G, 2008 Journal of Inflammation, 5:4). This molecule is also described in U.S. Pat. No. 5,643,893, which is incorporated herein by reference. LMP-420 is useful to preferentially inhibit IP-10 and/or eotaxin activity to treat or prevent AMD.

Any compound that inhibits the activity of CCR2, CCR3 or CCR5 is used in the invention. Compounds that inhibit the activity of eotaxin-1, -2 or -3 or the CCR2, CCR3, CCR5 receptors include organic small molecules such as piperidine derivatives such as those described in U.S. Pat. Nos. 6,984,651 and 6,903,115, and U.S. published applications 20050176708, 20050182094 and 20050182095; heterocyclic piperidines such as those described in U.S. Pat. No. 6,759,411; diphenyl-piperidine derivatives such as those described in U.S. Pat. No. 6,566,376; 2,5-substituted pyrimidine derivatives such as those described in U.S. Pat. No. 6,984,643; piperizinones such as those described in U.S. Pat. No. 6,974,869; bicycylic and tricyclic amines such as those described in U.S. Pat. No. 6,960,666; N-ureidoalkyl-piperidines such as those described in U.S. Pat. Nos. 6,949,546, 6,919,368, 6,906,066, 6,897,234, 6,875,776, 6,780,857, 6,627,629, 6,521,592 and 6,331,541; bicyclic diamines such as those described in U.S. Pat. No. 6,821,964; benzylcycloalkyl amines such as those described in U.S. Pat. No. 6,864,380; 2-substituted-4-nitrogen heterocycles such as those described in U.S. Pat. No. 6,706,735; ureido derivatives of poly-4-amino-2-carboxy-1-methylpyrrole compounds; bicyclic and bridged nitrogen heterocycles such as those described in U.S. published application 20050234034; azetidine derivatives such as those described in U.S. published application 20050222118; substituted fused bicyclic amines such as those described in U.S. published application 20050197373; substituted spiro azabicyclics such as those described in U.S. published application 20050197325; piperidine-substituted indoles or heteroderivatives thereof such as those described in U.S. published application 20050153979; piperidinyl and piperazinyl compounds substituted with bicyclo-heterocyclylalkyl groups such as those described in U.S. published application 20050090504; arylsulfonamide derivatives such as those described in U.S. published application 20050070582; 1-phenyl-1,2-diaminoethane derivatives such as those described in U.S. published application 20040063779; (N-{[2S]-4-(3,4-dichlorobenzyl)morpholin-2-yl}methyl)-N'[(2-methyl-2H-tetraazol-5-yl)methyl]urea) (see, e.g., Nakamura et al., Immunol Res., 33:213-222, 2006; N-{(3R)-1-[(6-fluoro-2-naphthyl)methyl]pyrrolidin-3-yl}-2-{1-[(3-methyl-1-oxidopyridin-2-yl)carbonyl]piperidin-4-ylidene}acetamide (see, e.g., Suzuki et al., Biochem. Biophys. Res. Commun., 339:1217-1223, 2006; N-{(3R)-1-[(6-fluoro-2-naphthyl)methyl]pyrrolidin-3-yl}-2-{1-[(5-hydroxy-3-methylpyridin-2-yl)carbonyl]piperidin-4-ylidene}acetamide hemifumarate (see, e.g., Morokata et al., J. Pharmacol. Exp. Ther., Dec. 9, 2005); bipiperidine amide antagonists of CCR3 such as those described in Ting et al., Bioorg. Med. Chem. Lett., 15:3020-3023, 2005; (S)-methyl-2-naphthoylamino-3-(4-nitrophenyl)propionate (see, e.g., Beasley et al., J. Allergy Clin. Immunol., 105: S466-S472, 2000; and the CCR3 antagonist compounds described in Fryer et al., J. Clin. Invest., 116:228-236, 2006.

CCR2 antagonists are described in WO99/07351, WO99/40913, WO00/46195, WO00/46196, WO00/46197, WO00/46198, WO00/46199, WO00/69432 or WO00/69815 or in Bioorg. Med. Chem. Lett., 10, 1803 (2000).

CCR3 antagonists are described in DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088.

CCR5 antagonists are described in WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605 or WO99/04794, WO99/38514 or in Bioorg. Med. Chem. Lett., 10, 1803 (2000)

The compositions of invention comprise a polynucleotide, a polypeptide, an antibody, a compound with means to inhibit the transcription, transcript stability, translation, modification, localization, secretion, or function of a polynucleotide or polypeptide encoding CCR3, CCR5 or CCR2 or eotaxin-1, -2 or -3. Antibodies of the invention can be monoclonal of polyclonal.

Compounds that inhibit the activity of IP-10 or the CXC receptors are used in the invention.

CXCR4 antagonists are described in WO00/66112. Small molecules, antibodies and other therapeutic agents that bind to CXCR3 receptor or modulate CXCR3 receptor activity are described in US application 20090285835 Antibodies which bind human CXCR3; 20090208486 Pharmaceutical composition comprising cxcr3 inhibitor; 20090169561 Anti-IP-10 antibodies and methods of use thereof; 20090143413 Thiazole Derivatives as CXCR3 Receptor Modulators; 20090131312 Non-natural chemokine receptor ligands and methods of use thereof; 20090030039 Piperidine Derivatives as CXCR3 Receptor Antagonists; 20090030012 Pyridine, Pyrimidine and Pyrazine Derivatives as CXCR3 Receptor Modulators; 20080312215 Substituted [1,4]-diazepanes as CXCR3 antagonists and their use in the treatment of inflammatory disorders; 20070197589 Cyclic quaternary amino derivatives as modulators of chemokine receptors; 20070172446 Synthetic chemokine receptor ligands and methods of use thereof; 20070149557 CXCR3 antagonists; 20070116669 Interferon-inducible protein-10 (IP-10 or CXCL10) chemokine analogs for the treatment of human diseases; 20070048801 CXCR3 is a gliadin receptor; 20060204498 Novel antagonists of CXCR3-binding CXC chemokines; 20060063763 Compounds and methods for modulating CXCR3 function; 20060040329 CXCL10-based diagnosis and treatment of respiratory illnesses; 20060036093 Pyrimidinone compounds; 20050272936 Imidazolium cxcr3 inhibitors; 20050113414 Piperidin-4-yl urea derivatives and related compounds as chemokine receptor inhibitors for the treatment of inflammatory diseases; 20050112688 Systems and methods for characterizing kidney diseases; 20050112119 Antibodies which bind human CXCR3; 20050070573 Aminoquinoline compounds; 20040209902 Aminoquinoline compounds; 20030158392 IP-10/Mig receptor designated CXCR3, antibodies, nucleic acids, and methods of use thereof; 20030119854 Compounds and methods for modulating CXCR3 function; 20020039578 Methods for treating disease with antibodies to CXCR3.

Small molecules, antibodies and other therapeutic agents that bind to CXCR3 receptor or modulate CXCR3 receptor activity are further described in U.S. Pat. No. 7,622,264 Methods for screening for modulators of CXCR3 signaling; U.S. Pat. No. 7,541,435 Antagonists of CXCR3-binding CXC chemokines; U.S. Pat. No. 7,427,487 Constitutively active CXCR3 G protein-coupled chemokine receptor and modulators thereof for the treatment of inflammatory disorders; U.S. Pat. No. 7,407,655 Method of inhibiting leukocytes with human CXC chemokine receptor 3 antibody; U.S. Pat. No. 7,405,275 Antibodies which bind human CXCR3; U.S. Pat. No. 7,378,524 Aminoquinoline compounds; U.S. Pat. No. 7,332,294 CXCL10-based diagnosis and treatment of respiratory illnesses; U.S. Pat. No. 7,244,555 Systems and methods for identifying organ transplant risk; U.S. Pat. No. 7,183,413 Aminoquinoline compounds; U.S. Pat. No. 7,138,229 Systems and methods for characterizing kidney diseases; U.S. Pat. No. 7,029,862 Method for identifying ligands, inhibitors or promoters of CXC chemokine receptor 3; U.S. Pat. No. 6,992,084 Compounds and methods for modulating CXCR3 function; U.S. Pat. No. 6,833,439 IP-10/MIG receptor designated CXCR3, nucleic acids and methods of use therefor; U.S. Pat. No. 6,686,175 IP-10/MIG receptor designated CXCR3, nucleic acids, and methods of use therefor; U.S. Pat. No. 6,559,160 Compounds and methods for modulating cxcr3 function; U.S. Pat. No. 6,184,358 IP-10/Mig receptor designated CXCR3, antibodies, nucleic acids, and methods of use therefor; U.S. Pat. No. 6,140,064 Method of detecting or identifying ligands, inhibitors or promoters of CXC chemokine receptor 3.

Small molecules, antibodies and other therapeutic agents that modulate the activity of IP-10 are described in US patent and patent applications 20090169561 Anti-IP-10 antibodies and methods of use thereof; 20080063646 Treatment Of Inflammatory Bowel Diseases With Anti-IP-10 Antibodies; 20070116669 Interferon-inducible protein-10 (IP-10 or CXCL10) chemokine analogs for the treatment of human diseases; 20070066523 Chemokine analogs for the treatment of human diseases; 20050191293 IP-10 antibodies and their uses; 20040197303 Design of chemokine analogs for the treatment of human disease; 20040141951 Cytokine inhibition of eosinophils; 20040096446 Methods for treating demyelinating diseases; 20040072237 Use of cytokines secreted by dendritic cells; 20040009503 Immune modulatory activity of human ribonucleases; 20030166589 Method and pharmaceutical composition for the treatment of multiple sclerosis; 20030158392 IP-10/Mig receptor designated CXCR3, antibodies, nucleic acids, and methods of use therefore; U.S. Pat. No. 7,091,310 chemokine analogs for the treatment of human disease.

The compositions of invention comprise a polynucleotide, a polypeptide, an antibody, a compound with means to inhibit the transcription, transcript stability, translation, modification, localization, secretion, or function of a polynucleotide or polypeptide encoding IP-10 or CXCR3.

H1 receptor antagonists have been suggested for the treatment of AMD (For example, WO 2009067317) and treatment with H1 receptor antagonists indirectly act on the expression of IP-10. By contrast, described herein is the direct inhibition of IP-10, which has the CXCR3 receptor. Thus, the pathways of inhibition are different.

EXAMPLES

Example 1

IP-10 and Eotaxin Are Biomarkers For Age-Related Macular Degeneration

AMD patients and control subjects recruited for serum cytokine measurement. Seventy-eight subjects with phenotypic and clinical evidence of AMD were recruited into the study and classified according to the Age-Related Eye Disease Study (AREDS) into AREDS stage 1 (early AMD), AREDS stage 3 (intermediate dry AMD), geographic atrophy (defined as geographic loss of photoreceptor-RPE-choriocapillaris) and neovascular AMD. All subjects were examined by slit-lamp biomicroscopy, optical coherence tomography, fundus photography and fluorescein angiography (when indicated). Eighteen age-matched patients with no phenotype of AMD and no family history of AMD were recruited as control subjects and were examined with similar methods. All subjects were given a simple questionnaire regarding their smoking history, and whether they had or were treated for hypertension and hypercholesterolemia. Inclusion criteria included minimal age of 55, and willingness to participate in the study. Exclusion criteria were very strict. Subjects with the following systemic conditions were excluded from the study: any cancer, inflammatory conditions including collagen vascular disease, arthritis, taking non-steroidal or steroidal anti-inflammatory or immune-modulating products, diabetes mellitus, kidney or liver disease, vascular disease such as stroke, blood dyscrasia and recent surgery (<90 days). The following ocular conditions were also excluded: history of glaucoma or glaucoma suspect, using topical anti-inflammatory products, history of central or branch retinal vein occlusion, diabetic retinopathy, retinal detachment, and other chronic macular disease, recent cataract extraction (<90 days). Patients were asked to sign a detailed consent form and blood samples were withdrawn for plasma and serum collection.

Serum samples preparation and running Bio-plex for cytokine measurement. Blood samples were allowed to clot for at least 30 minutes at room temperature or at 4° C. overnight, and then centrifuged 1000×g for 10 minutes to remove cellular components. Sera were taken and stored at −20° C. Bio-plex components including the validation kit (Bio-plex, V4), calibration kit and human 27-plex were purchased from Bio-Rad, (Hercules, Calif.). Samples (50 µl) were diluted 4-fold with human serum diluent and the final results were adjusted for the dilution factor. Each sample was run in duplicate. Serum samples were processed using a multi-cytokine Bio-Plex Suspension Array System (Bio-Rad, CA) according to the manufacturer's protocol.

Statistical Analysis. GraphPad Prism 4 and Prism's statistics were used to plot graphs and perform statistics. Since serum samples were not distributed in a Gaussian fashion, a Mann-Whitney test was used to test the statistical difference between the AMD group and the control group. A non-parametric age-matched pair Wilcoxon signed rank sum test was also used to compare the significant differences in cytokine levels between AMD and control groups. This excluded age as a compounding factor.

Tissue specimens. Eyes of patients who had recently expired and were undergoing planned autopsy were enucleated at autopsy. Eyes were preserved in 4% buffered formaldehyde solution, embedded in paraffin and sectioned according to the protocol established at Duke Hospital, Department of Pathology. H&E stains were prepared and read by one of us (ADP) and evaluated for subretinal lesions that would be characteristic of AMD. The medical records of the patient were also available. Ocular findings on H&E were correlated with the stage of AMD derived from the patient's medical record. Early stage AMD (AREDS 1) was characterized by presence of hard drusen between the RPE layer and the Bruch's membrane. Intermediate stage AMD showed confluent drusen with thickening and deposits within the inner Bruch's layer indicative of basal laminar/linear desposits and soft drusen. The RPE layer and choriocapillaris remained intact. Geographic atrophy was characterized by the degeneration of the photoreceptors, RPE and choriocapillaris layers and presence of a transition zone. Neovascular AMD was characterized by clear presence of new vessels on the inner side of the Bruch's membrane with associated RPE or photoreceptor degeneration. Control eyes showed normal Bruch's anatomy with absence of basal linear deposits or hard drusen within the macular area. The foveal area was also intact.

Immunohistochemistry. Tissue slides were deparaffinized by incubating them at 60° C. for 30 minutes to 1 hour and rehydrated through a series of alcohol steps. Slides were initially subjected to antigen retrieval by heating at 100° C. in an antigen unmasking solution (Vector Laboratories, Burlingame, Calif.), blocked with 3% albumin bovine Cohn fraction V (Sigma, St. Louis, Mo.) and avidin (Vector Lab.) for 1 hour. Prior to adding the primary antibody, slides were incubated with biotin for 15 min, and incubated with anti-human IP-10 or anti-human Eotaxin antibodies (both from R&D Systems, Minneapolis, Minn.) at 1:200 dilution overnight at 4° C. Slides were washed in PBS and incubated with biotinylated anti-goat IgG (1:250) for 1 hour, stained with the Vectastain ABC.AP kit with Vector Red (Vector Labs.) and counterstained with hematoxylin (Vector Labs.).

Analysis of serum cytokines in different stages of AMD. A total of 96 subjects were included in this study. Table 1, which is a study of serum cytokines of AMD, summarizes the clinical data of all subjects. There were between 18-20 subjects in each group. The distribution of smokers, hypertension and elevated cholesterol levels in the study group are indicated.

Table 2 shows Serum Cytokine concentrations (pico grams) determined from different stage of AMD patients. Mean serum level pg/ml±SEM. Abbreviations: C, control subjects, without AMD; I, AREDS stage 1, early AMD; III, AREDS stage 3, intermediate AMD; GA, geographic atrophy, CNV, neovascular AMD.

Table 3 shows age matched pair comparison of serum eotaxin and IP-10 concentrations between no AMD (AMD=0) and AMD groups (AMD>0) and no AMD vs AREDS stage 1 AMD groups. (A) Mean concentrations of each age group for eotaxin are shown for control subjects (AMD=0), subjects with AMD (AMD>0), and the difference between the two groups. (B) Mean concentrations of each age group for eotaxin are shown for control subjects (AMD=0), subjects with stage 1 AMD (AMD=1) and the difference between the two groups. (C) Mean concentrations of each age group for IP-10 are shown for control subjects (AMD=0), subjects with AMD (AMD>0), and the difference between the two groups. (D) Mean concentrations of each age group of IP-10 are shown for control subjects (AMD=0), subjects with stage 1 AMD (AMD=1) and the difference between the two groups.

The concentrations of twenty cytokines are shown in Table 3. The concentrations of five cytokines (IL-2, IL-15, IL-17, FGF and GM-CSF) were below 0.2 pg/ml, the lowest limit of detection in the standard curve. These cytokines were regarded as undetectable. RANTES and PDGF-bb concentrations exceeded the upper limit of the standard curves and were excluded from the study. Of the twenty cytokines studied, only IP-10 and eotaxin were significantly elevated in AMD study group. These two cytokines were selected for further study and analysis.

Serum eotaxin and IP-10 levels are significantly increased in AMD patients. The mean serum concentrations and individual distributions of Eotaxin and IP-10 are shown in FIG. 1. The Man-Whitney test was used to detect significant differences between the control group and each of AMD subgroups. Eotaxin was significantly increased in AREDS stages 1, 3 and GA ($P<0.02$, $P<0.007$ and $P<0.005$, respectively), but not in neovascular AMD (CNV; $P<0.07$). There were no differences in eotaxin concentrations among AMD subgroups. IP-10 was increased in AREDS stage 1 ($P<0.004$) and remained high in all stages of AMD. In AREDS stage 3, IP-10 levels reached the peak ($P<0.002$). In advanced AMD, IP-10 levels were lower in subjects with neovascular AMD than in ARDS stage 3 and GA ($P<0.05$ and $P<0.03$, respectively).

Figure 2:
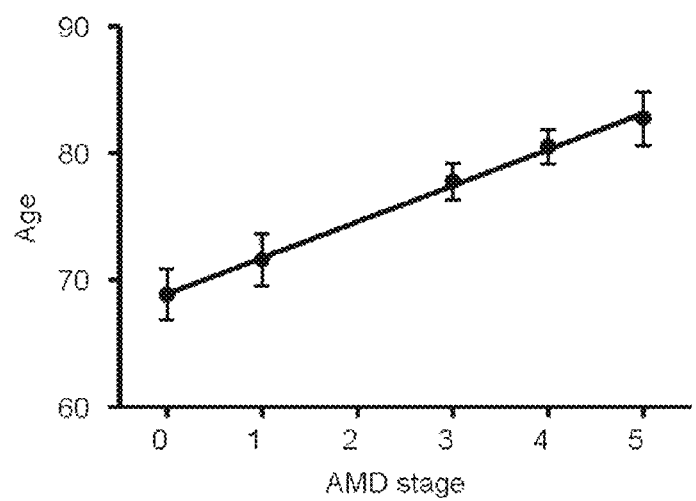
FIG. 2 is a line graph depicting the correlation between age and AMD of stage (control subjects are stage 0).

Age-matched pair analysis of IP-10 and eotaxin in subjects with AMD. Subjects in the control group ranged between 59 to 85 years of age. There was a similar wide span of ages in the four groups of patients with AMD. However, mean ages were higher in the more severe AMD groups. To illustrate this, a numeric code was assigned for the stages of AMD with "0" assigned to no AMD, "1" to AREDS stage 1, "3" to AREDS stage 3, "4" to neovascular AMD, and "5" to GA (FIG. 2). This strong relationship between age and level of AMD required that statistical methods be used to remove age as a factor when studying cytokine levels and AMD stage. To accomplish this, age-matched groups were formed and levels of eotaxin and IP-10 were compared only for patients with the same age (within one year). To avoid any assumptions about normality, the non-parametric matched pair Wilcoxon signed rank sum test was used. The null hypothesis was that for subjects of the same age, the level of cytokine (eotaxin or IP-10) is the same for control subjects and those with any stage of AMD. There were 12 age groups formed, each of which contained control subjects (AMD=0) and subjects with AMD (AMD>0). The average cytokine level was calculated for each age group. The difference between these two average cytokine levels was then determined according to the following equation:

$$\text{Difference}_{same\ age} = \text{mean cytokine}(AMD>0) - \text{mean cytokine}(AMD=0).$$

Results are shown in Table 4.

Table 4 shows the distribution of IP-10 in the Macular and Subjacent Choroid. Table 5 shows the distribution of Eotaxin in the Macular and Subjacent Choroid. Tables 4 and 5 show grading scale for the expression of interferon-induced protein-10 (IP-10) and eotaxin in the macula and subjacent choroid. 0, no expression; 1, very faint expression; 2, moderate staining; 3, strong staining; Focal, focal expression. Abbreviations: AMD, age-related macular degeneration; GA, geographic atrophy; CNV, choroidal neovascularization (neovascular AMD); NFL, nerve fiber layer; GCL, ganglion cell layer; IPL, inner plexiform layer; INL, inner nuclear layer; OPL, outer plexiform layer; ONL, outer nuclear layer; POS, photoreceptor outer segments; RPE, retinal pigment epithelium; BLD, basal linear/laminar deposits; Choroid EC, choroidal endothelial cells; Ch. stroma, choroidal stromal cells; Neovasc EC, neovascular endothelial cells; RPE—outside, RPE cells outside the area of choroidal neovascularization; RPE—neovascular, RPE cells within the area of choroidal neovascularization.

Almost all differences were positive. The absolute values of the differences were ranked and then the ranks of the negative differences were summed. Overall, most of the differences among age-matched groups were positive (AMD>0–AMD=0), indicating that the level of the cytokine in any AMD category was higher than those in the control group. Table 4A shows the concentrations of eotaxin for control subjects (AMD=0), for subjects with any stage AMD (AMD>0), and their respective difference in an age-matched manner. The Wilcoxon statistical tables (Davis et al., 2005 Archives of Ophthalmology, 123: 1484-1498) indicate that the probability of such a distribution is $p<0.005$. Eotaxin levels at any stage AMD were higher than in control subjects with no AMD.

Next, it was determined if elevated levels of eotaxin could be used as a biomarker for early onset of AMD (AREDS stage 1). This involved comparing age-matched groups of subjects with AMD=0 and AMD=1. There were 10 such groups where the age in each group was the same (within two years) (Table 4B). The difference between eotaxin levels for AREDS stage 1 (AMD=1) and control (AMD=0) was calculated according to the following formula:

$$\text{Difference}_{same\ age} = \text{eotaxin}(AMD=1) - \text{eotaxin}(AMD=0)$$

Table 4B shows the concentrations of eotaxin for age-matched control subjects (AMD=0), subjects with AREDS stage 1 (AMD=1) and their differences. Results indicate that differences were dominantly positive with the largest differences being always positive. The Wilcoxon table shows the probability of such a distribution occurring by chance is $p<0.05$. Eotaxin levels in subjects with AREDS stage 1 AMD are significantly higher than those in control subjects with no AMD. A similar analysis was performed for IP-10 using the same age-matched groups.

Table 4C shows the concentrations for IP-10 for control subjects (AMD=0), subjects with any AMD (AMD>0) and their differences. The concentrations of IP-10 for subjects with any stage of AMD were significantly higher than those in the control group. The Wilcoxon table shows the probability of such a distribution occurring by chance is $p<0.025$.

Immunohistochemical (IHC) localization of IP-10 and eotaxin in eyes with or without AMD. The expression of IP-10 and eotaxin in autopsy eyes of patients with different stages of AMD and age-matched non-AMD controls was determined using IHC staining. Staining intensity was graded on a scale of 0 to 3: 0, no expression; 1, very faint staining (visible only at high magnification); 2, moderate staining (easily visible at intermediate magnification); 3, strong staining (visible at low magnification). Results for all of the eyes are presented in Table 4 (IP-10 scores) and Table 5 (eotaxin scores). Scoring of staining intensity was done by two investigators and results are a consensus of their observations. Both IP-10 and eotaxin were expressed in the neurosensory retina in the nerve fiber layer, ganglion cell layer (GCL), inner nuclear layer (INL), outer nuclear layer (ONL), and photoreceptor outer segments (POS); staining intensity was variable between eyes within each group, and there was no consistent difference in staining among the eyes with or without AMD, as shown in Tables 4 and 5 and FIGS. 3 and 4. For all eyes, negative controls were performed for IP-10 and eotaxin using non-immune IgG isotype in place of the primary antibody. The negative control slides uniformly lacked stain. Despite variation in staining intensity for IP-10 among eyes within each group, there were definite differences in IP-10 expression in control eyes and those with AMD. As shown in FIG. 3, there was enhanced expression of IP-10 in the RPE of eyes with early AMD, GA, and CNV. IP-10 accumulated focally within the layer of basal linear/laminar deposit in GA and CNV, and it was uniformly and strongly expressed by neovascular endothelial cells and within the connective tissue matrix associated with the CNV. There was also variation in staining intensity for eotaxin among eyes within each group, but again there were distinct differences in eotaxin expression in control and AMD eyes. FIG. 4 illustrates enhanced expression of eotaxin in the RPE of eyes with early AMD, GA, and CNV. There was accumulation of eotaxin within the basal linear/laminar deposit in all stages of AMD, though the staining was patchy (focal) and less than that observed for IP-10. Similar to the results for IP-10, eotaxin expression by neovascular endothelial cells was observed. There was often eotaxin within the connective tissue matrix associated with CNV, but the expression of eotaxin was more focal and the staining less intense than for IP-10 in this tissue compartment (for example, compare the staining for IP-10 in FIG. 3H with that for eotaxin in FIG. 4H).

FIG. 5 illustrates enhanced expression of CCR3 in the RPE of eyes with early AMD, GA, and CNV. CCR3 expression is detected in some retinal ganglion (RGC) cells, INL, and in endothelial cells associated with choroidal neovascular membrane (CNVM). Enhanced expression of the CCR3 receptor in the eyes of patients with early AMD suggests that the CCR3-eotaxin pathway is implicated in the disease and that receptors antagonists can be used for the treatment of AMD.

TABLE I

Clinical profile of study subjects.

|  | CONTROL | AREDS I | AREDS III | GA | CNV |
|---|---|---|---|---|---|
| Number of subjects | 18 | 20 | 19 | 20 | 19 |
| Number of male | 9 | 6 | 7 | 6 | 5 |
| Number of female | 9 | 14 | 12 | 14 | 14 |
| Age | 69 ± 2 | 72 ± 2 | 78 ± 1 | 83 ± 2 | 81 ± 1 |
| Smoker - no | 12 | 15 | 9 | 11 | 12 |
| Smoker - former | 5 | 4 | 9 | 5 | 5 |
| Smoker - yes | 1 | 1 | 1 | 4 | 2 |
| Hypertension - no | 8 | 9 | 5 | 10 | 7 |
| Hypertension - yes | 10 | 11 | 14 | 10 | 12 |
| High cholesterol - no | 11 | 12 | 12 | 16 | 11 |
| High cholesterol - yes | 7 | 8 | 7 | 4 | 8 |

Subjects' ages are shown as mean ± SEM. Smoking, hypertension and cholesterol histories are included. Abbreviations: Control, without AMD; AREDS 1, early AMD; AREDS 3, intermediate AMD; GA, geographic atrophy, CNV, neovascular AMD.

TABLE 2

|  | C | I | III | GA | CNV |
|---|---|---|---|---|---|
| IL-1beta | 4.5 ± 1.4 | 9.0 ± 4.5 | 15 ± 13 | 5.1 ± 2.6 | 1.0 ± 0.2 |
| IL-1ra | 209 ± 68 | 288 ± 86 | 380 ± 185 | 152 ± 28 | 197 ± 77 |
| IL-4 | 1.7 ± 0.2 | 1.6 ± 0.2 | 2.0 ± 0.4 | 1.5 ± 0.2 | 1.9 ± 0.6 |
| IL-5 | 0.7 ± 0.1 | 0.9 ± 0.1 | 0.4 ± 0.1 | 0.8 ± 0.1 | 0.5 ± 0.1 |
| IL-6 | 22 ± 5 | 21 ± 9 | 6.1 ± 2.0 | 11 ± 3 | 6.0 ± 1.8 |
| IL-7 | 5.4 ± 0.8 | 3.8 ± 0.5 | 5.1 ± 0.6 | 5.1 ± 0.7 | 4.5 ± 0.6 |
| IL-8 | 510 ± 181 | 339 ± 223 | 221 ± 170 | 250 ± 161 | 151 ± 109 |
| IL-9 | 101 ± 76 | 74 ± 50 | 26 ± 5 | 398 ± 205 | 265 ± 161 |
| IL-10 | 7.0 ± 4.2 | 6.0 ± 0.9 | 3.3 ± 0.7 | 8.0 ± 2.1 | 2.9 ± 0.9 |
| IL-12 (p70) | 3.2 ± 1.0 | 7.7 ± 1.5 | 3.4 ± 0.7 | 9.1 ± 2.0 | 10 ± 5 |
| IP-10 | 466 ± 78 | 966 ± 167 | 1491 ± 473 | 1036 ± 193 | 745 ± 168 |
| IL-13 | 2.6 ± 0.5 | 11 ± 2 | 6.1 ± 2.0 | 11 ± 3 | 1.8 ± 0.2 |
| Eotaxin | 71 ± 10 | 137 ± 27 | 125 ± 14 | 139 ± 17 | 102 ± 11 |
| G-CSF | 47 ± 16 | 32 ± 5 | 41 ± 8 | 28 ± 4 | 24 ± 5 |
| INF-gamma | 59 ± 7 | 84 ± 10 | 88 ± 28 | 64 ± 7 | 40 ± 6 |
| MCP-1 | 44 ± 11 | 29 ± 6 | 22 ± 5 | 18 ± 3 | 27 ± 6 |

TABLE 2-continued

|  | C | I | III | GA | CNV |
|---|---|---|---|---|---|
| MIP-1alpha | 39 ± 12 | 19 ± 6 | 53 ± 38 | 26 ± 7 | 16 ± 3 |
| MIP-1beta | 335 ± 58 | 267 ± 50 | 270 ± 41 | 242 ± 54 | 190 ± 38 |
| TNF-alpha | 37 ± 8 | 31 ± 4 | 28 ± 6 | 28 ± 4 | 22 ± 3 |
| VEGF | 188 ± 94 | 135 ± 20 | 143 ± 30 | 245 ± 73 | 105 ± 16 |

TABLE 3

(A)

| Age Group | Eotaxin AMD = 0 | Eotaxin AMD > 0 | Difference AMD > 0 - AMD = 0 |
|---|---|---|---|
| 58-59 | 13.7 | 93.3 | 79.6 |
| 60 | 45.8 | 202.4 | 156.5 |
| 62 | 152.0 | 121.0 | -31.0 |
| 65 | 95.0 | 129.8 | 34.8 |
| 67 | 61.4 | 241.6 | 180.2 |
| 68-69 | 97.4 | 119.7 | 22.3 |
| 70 | 72.4 | 177.0 | 104.5 |
| 72 | 45.2 | 151.8 | 106.5 |
| 74 | 25.2 | 71.2 | 46.0 |
| 80 | 74.7 | 129.1 | 54.4 |
| 83 | 92.9 | 126.6 | 33.8 |
| 85 | 64.5 | 183.8 | 119.3 |
|  |  |  | P < 0.005 |

(B)

| Age Group | Eotaxin AMD = 0 | Eotaxin AMD = 1 | Difference AMD = 1 - AMD = 0 |
|---|---|---|---|
| 58-59 | 13.7 | 93.3 | 79.6 |
| 60-62 | 98.9 | 86.6 | -12.3 |
| 65 | 95.0 | 129.8 | 34.8 |
| 67-69 | 73.4 | 46.0 | -27.4 |
| 70 | 72.4 | 267.9 | 195.5 |
| 72 | 45.2 | 151.8 | 106.5 |
| 73-74 | 25.2 | 260.0 | 234.8 |
| 80 | 74.7 | 49.6 | -25.1 |
| 83 | 92.9 | 34.4 | -58.5 |
| 85 | 64.5 | 543.0 | 478.6 |
|  |  |  | P < 0.05 |

(C)

| Age Group | IP-10 AMD = 0 | IP-10 AMD > 0 | Difference AMD > 0 - AMD = 0 |
|---|---|---|---|
| 58-59 | 166.9 | 527.6 | 360.7 |
| 60 | 264.6 | 432.0 | 167.4 |
| 62 | 505.8 | 791.8 | 286.0 |
| 65 | 808.2 | 1029.4 | 221.2 |
| 67 | 676.9 | 509.0 | -167.8 |
| 68-69 | 190.2 | 717.0 | 526.8 |
| 70 | 1228.0 | 463.3 | -764.7 |
| 72 | 355.6 | 564.7 | 209.1 |
| 74 | 254.3 | 4510 | 196.7 |
| 80 | 404.5 | 1405.4 | 1001.0 |
| 83 | 455.1 | 1007.6 | 552.5 |
| 85 | 261.9 | 1563.8 | 1301.9 |
|  |  |  | P < 0.025 |

(D)

| Age Group | IP-10 AMD = 0 | IP-10 AMD = 1 | Difference AMD = 1 - AMD = 0 |
|---|---|---|---|
| 58-59 | 166.9 | 529.6 | 360.7 |
| 60-62 | 385.2 | 86.6 | 220 |
| 65 | 808.2 | 1029.4 | 221.2 |
| 67-69 | 514.6 | 753.4 | 238.8 |
| 70 | 1228.0 | 657.1 | -570.9 |
| 72 | 355.6 | 564.7 | 209.1 |
| 73-74 | 254.3 | 3600.0 | 3345.7 |
| 80 | 404.5 | 1429.1 | 1024.6 |
| 83 | 455.1 | 1558.0 | 1102.8 |
| 85 | 261.9 | 893.4 | 631.5 |
|  |  |  | P < 0.025 |

TABLE 4

Distribution of IP-10 in the Macular and Subjacent Choroid

| Case # | NFL | GCL | IPL | INL | OPL | ONL | POS | RPE | BLD | Choroid EC | Ch. Stroma |
|---|---|---|---|---|---|---|---|---|---|---|---|
| Control |  |  |  |  |  |  |  |  |  |  |  |
| 1 | 2 | 2 | 1 | 0 | 1 | 1 | 3 | 0 |  | 0 | 1 |
| 2 | 1 | 2 | 0 | 0 | 1 | 0 | 2 | Focal 1 |  | 0 | 1 |
| 3 | 2 | 2 | 1 | Focal 1 | 0 | 0 | 3 | Focal 2 |  | Focal 1 | Focal 1 |
| 4 | 2 | 3 | 2 | 1 | 1 | 0 | 2 | 0 |  | 1 | 2 |
| 5 | Focal 2-3 | 3 | 1 | 1 | 1 | 1 | 3 | Focal 2-3 |  | 1 | 2 |
| 6 | 1 | 2 | 1 | 0 | 1 | 0 | 1 | Focal 1-2 |  | 0 | 0 |
| 7 | 0 | 3 | 1 | 1, Focal 2 | 0 | Focal 1 | 2 | 0 |  | 0 | 2 |
| 8 | 1 | 3 | 1 | 1 | 1 | 0 | 1 | Focal 1-2 |  | 0 | Focal 1 |

TABLE 4-continued

Distribution of IP-10 in the Macular and Subjacent Choroid

Early AMD

| | | | | | | | | | | | |
|---|---|---|---|---|---|---|---|---|---|---|---|
| 11 | 2 | 3 | 2 | 1 | 1 | 1 | 3 | 3 | 0 | 2 | 3 |
| 12 | 2 | 3 | 1 | Focal 0-1 | 0 | 1 | 2 | Focal 3 | Focal 2 | 0 | Focal 1 |
| 13 | 3 | 3 | 2 | 0 | 1 | 1 | 3 | Focal 2 | 0 | 0 | 2 |
| 14 | 2 | 3 | 1 | 1 | 0 | 0 | 2 | 2 | 0 | 0 | 1 |
| 15 | 2 | 3 | 2 | 1 | 2 | 1 | 3 | 2 | 0 | 1-2 | 2 |
| 16 | 1 | 3 | 2 | 2 | 2 | 1 | 3 | 1 | 0 | 1 | 1 |
| 17 | 2 | 3 | 2 | 1 | 2 | 2 | 2 | 3, Focal 4 | Focal 1 | 0 | 1 |
| 18 | 2 | 3 | 1 | Focal 1-2 | 1 | 1 | 2 | Focal 1 | 0 | 0 | 2 |

GA

| | | | | | | | | | | | |
|---|---|---|---|---|---|---|---|---|---|---|---|
| 21 | 2 | 2 | 1 | 0 | 0 | 0 | — | 1 | 0 | 0 | 2 |
| 22 | 2 | 3 | 2 | 1 | 0 | — | — | 2 | Focal 1-2 | 0 | 0 |
| 23 | 2 | 3 | 2 | 1 | 1 | 1 | 3 | 3 | Focal 3 | 1 | 1 |
| 24 | 2 | 3 | 2 | 1 | 2 | 0 | 3 | 2 | Focal 3 | Focal 1 | 1 |

| CNV | | | | | | | RPE outside | RPE CNV area | | Choroid EC | Neovasc EC | |
|---|---|---|---|---|---|---|---|---|---|---|---|---|
| 27 | 1 | 3 | 2 | 1 | 2 | 1 | 3 | 3 | Focal 2 | Focal 3 | 1 | 2 | 1-2 |
| 28 | 3 | 3 | 1 | 2 | 2 | Focal 1-2 | 2 | 3, Focal 4 | Focal 1-2 | Focal 2 | 1 | 3 | 2 |
| 29 | 3 | 3 | 1 | 1 | 1 | 1 | 3 | 3 | Focal 1-2 | Focal 3 | 1 | 3-4 | 2 |
| 30 | 2 | 3 | 1 | 1 | 1 | Focal 1 | 1 | 2-3 | Focal 2-3 | 2 | 1 | 2 | 2 |
| 31 | 1 | 2 | 1 | 1 | 1 | Focal 1 | 2 | 1 | Focal 3 | 1, Focal 3 | 1 | 3 | 3 |
| 32 | 2 | 3 | 1 | 1 | 0 | Focal 1 | 2 | 1, Focal 2 | 1, Focal 2 | Focal 3 | 1 | 2, Focal 3 | 1 |

TABLE 5

Distribution of Eotaxin in the Macular and Subjacent Choroid

| Case # | NFL | GCL | IPL | INL | OPL | ONL | POS | RPE | BLD | Choroid EC | Ch. Stroma |
|---|---|---|---|---|---|---|---|---|---|---|---|
| Control | | | | | | | | | | | |
| 1 | 3 | 3 | 1 | 1 | 2 | 1 | 1 | 0 | | 1 | 2 |
| 2 | 3 | 3 | 1 | 1 | 2 | 1 | 2 | 0 | | Focal 1 | 2 |
| 4 | 0 | 3 | 1 | 1 | 1 | 1 | 3 | 1 | | 2 | |
| 6 | 0 | 2 | 0 | 1 | 0 | 0 | 2 | 0 | | 2 | |
| 7 | 0 | 3 | 1 | 1, Focal 2 | 0 | 1 | 2 | 0 | | 1-2 | 1 |
| 8 | 0 | 1 | 0 | 1 | 0 | 0 | 0 | 0 | | 0 | 0 |
| 9 | 1 | 2 | 1 | Focal 1 | 1 | Focal 1 | 1 | 0 | | 1 | 1 |
| 10 | 1 | 2 | 0 | 1 | 0 | 1 | 3 | 1 | | 1 | |
| Early AMD | | | | | | | | | | | |
| 12 | 0 | 2 | 0 | 1 | 0 | 1 | 0 | Focal 1 | Focal 2 | 1 | 2 |
| 13 | 0 | 3 | 1 | 2 | 1 | 1 | 3 | 2 | 3 | 2 | 2 |
| 14 | 0 | 0 | 0 | 0 | 0 | 0 | 0 | 0 | 3 | 1 | 0 |
| 16 | 0 | 3 | 0 | 1 | 0 | 0 | 3 | 3 | Focal 1 | 2 | 2 |
| 19 | 0 | 3 | 1 | 2 | 1 | 0 | 3 | 2 | 3 | 2 | 1 |
| 20 | 0 | 3 | 1 | 2 | 2 | 2 | 3 | 2 | 3 | 2 | 2 |
| GA | | | | | | | | | | | |
| 22 | 2 | 2 | 0 | 1 | 1 | 1 | 3 | 1 | Focal 2 | 2 | 2 |
| 24 | 0 | 3 | 0 | 2 | 0 | 1 | 3 | 3 | Focal 3 | 2 | 2 |
| 25 | 0 | 1 | 0 | 0 | 0 | 0 | 0 | 1 | Focal 2 | 1 | 1 |
| 26 | 0 | 0 | 0 | 0 | 0 | 0 | 0 | 0 | 1-2 | 0 | 0 |

| CNV | | | | | | | RPE outside | RPE CNV area | | Choroid EC | Neovasc EC | |
|---|---|---|---|---|---|---|---|---|---|---|---|---|
| 27 | 0 | 1 | 0 | 1 | 0 | 0 | 0 | 1 | Focal 3 | 0 | Focal 2 | 2 | 0 |
| 29 | 2 | 3 | 1 | 2 | 2 | 3 | 3 | 2, Focal 3 | 1 | 0 | 2, Focal 3 | 3 | 2 |
| 30 | 0 | 3 | 2 | 2 | 1 | 2, Focal 3 | 3 | 1, Focal 2 | 1, Focal 2 | Focal 1 | 2 | 3 | 2 |
| 31 | 3 | 3 | 1 | 2 | 1 | Focal 3 | 2 | 2 | 3 | 1, Focal 2 | 2-3 | 3 | 2 |
| 32 | 1 | 3 | 1 | 2 | 1 | 2, Focal 3 | 2 | 2 | 2, Focal 3 | 2, Focal 3 | 1, Focal 2-3 | 3 | 2 |
| 33 | 0 | 3 | 2 | 2 | 1 | 1, Focal 3 | 3 | 2 | 2 | Focal 2 | 2, Focal 3 | 3 | 2 |
| 34 | 1 | 3 | 1 | 2 | 2 | 1, Focal 3 | 3 | 2 | 2 | Focal 1 | 1 | 2, Focal 3 | 1 |

TABLE 6

Suitable inhibitors of IP-10 and/or eotaxin.

| Molecule Name | Activity | Reference |
|---|---|---|
| DPC 168 | CCR3 antagonist | Bioorg med chem. Lett; 2992-2997 (2007) |
| BMS570520 | CCR3 antagonist | Bioorg Med chem. Lett, 12, 1785 (2002) |
| Ki 19003 | CCR3 antagonist | J. Pharmacol Sci 112(2), 203-13, (2010) |
| SB 328437 | CCR3 antagonist | J. Biol Chem, 275, 36626 (2000) |
| UCB 35625 | CCR3 antagonist | J. Biol Chem, 275, 25985 (2000) |
| GW701897 | CCR3 antagonist | J Clin Invest. Jan. 4; 116(1): 228-236, (2006) |
| YM-344031 | CCR3 antagonist | Biochemical and Biophysical Research Communications. January 339(4) p1217-1223 (2006) |
| CCR3 antagonist | CCR3 antagonist | Immunological Research; 33(3), 213-221 (2005) |
| GW766994 | CCR3 antagonist | WO03082292 |
| NBI-74330, T487 | CXCR3 antagonist | WO02083143 |
| NSC 651016 | CCR1, CCR3, CCR5, and CXCR4 | Antivir. Res. 27: 335-354 (1995) |
| LMP 420 | IP-10 antagonist | PLoS Med. September; 2(9): e315 (2005) |
| AZD3778 | CCR3 antagonist | Respiratory Research 11:17 (2010) |
| T0906487 | CXCR3 antagonist | Cytokine 15, 113-121 (2001) |
| AMG487 | CXCR3 antagonist | Bioorganic & Medicinal Chemistry Letter, 17, 12, 3339-3343 (2007) |
| TAK 779 | CCR5 and CXCR3 antagonist | WO/2000/010965 |
| NBI-74330 | CXCR3 antagonist | WO02083143100e; Arterioscler Thromb Vasc Biol 28; 251-257 (2008). |

Example 2

Increased Systemic Expression of IP-10 in Subjects with AMD

In addition to searching for cytokines of potential pathogenic relevance in AMD, a secondary purpose was to determine if serum cytokine levels could serve as biomarkers to predict the early onset of AMD. Elevation of serum IP-10 has been proposed as a biomarker to predict the outcome in many human diseases such as severe acute respiratory distress syndrome (Tang N L et al., 2005 Clinical chemistry, 51:2333-2340) coronary artery disease, especially in patients with restenosis (Kawamura A et al., 2003 Circ J, 67:851-854) and as a risk factor for renal allograft failure (Rotondi M, et al. 2004 Am J Transplant, 4:1466-1474).

Serum IP-10 level has been reported to increase in aging (Miles E A, et al., 2008 Atherosclerosis, 196:298-305). As described herein, both serum IP-10 and eotaxin concentrations were significantly increased in AMD patients. As described below, aging was significantly correlated with progression of AMD as shown in FIG. 2. Age-matched paired-comparison studies were performed to exclude age as a factor in the elevation of IP-10 in the patients with AMD. Both IP-10 and eotaxin were significantly elevated in patients with AREDS stage 1 (early AMD) compared with the control group. Thus, serum levels of IP-10 and eotaxin serve as biomarkers for early AMD, when vision is unaffected and prior to the appearance of any significant phenotypic changes in the retina.

The increased expression of certain interferon γ-inducible chemokines (CMC chemokines) is associated with chronic inflammatory disease, including ophthalmic diseases such as chronic dry eye syndrome. These chemokines include IP-10, MIG (monokine induced by interferon γ), and TAC (interferon-inducible T-cell alpha chemoattractant). These chemokines bind to the CXCR3 receptor expressed on activated T cells and NK cells.

Figure 6A:
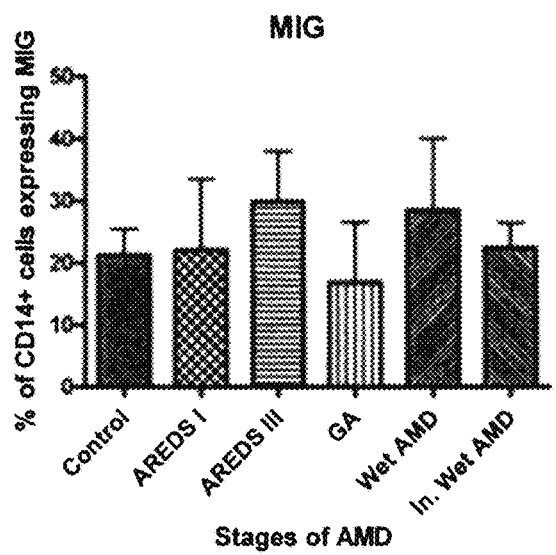
FIGS. 6A, 6B and 6C are bar graphs depicting the percentage of $CD14^+$ cells expressing the interferon γ-inducible chemokines IP-10 (IP-10/CXCL10), MIG (monokine induced by interferon γ or MIG/CXCL9) and TAC (interferon-inducible T-cell alpha chemoattractant or I-TAC/CXCL11), in subjects with various stages of AMD (n=2-5). Patients were classified according to the following groups: Control: control subject—no phenotypic evidence of AMD; AREDS I: AREDS stage 1 minimal drusen (early AMD); AREDS III: AREDS stage 3 confluent drusen (intermediate dry AMD); GA: geographic atrophy; Wet AMD: subjects with first presentation of AMD; Inactive Wet AMD: subjects who received intravitreal ranibizumab (Lucentis™) or Avastin™ (bevasizumab; humanized anti-VEGF antibody) treatment and no longer exhibited active disease based on clinical examination and non-invasive testing including optical coherence tomography.
Figure 6B:
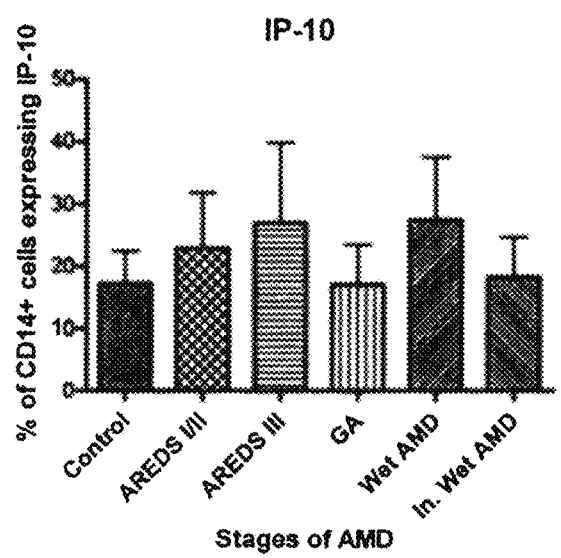
Figure 6C:
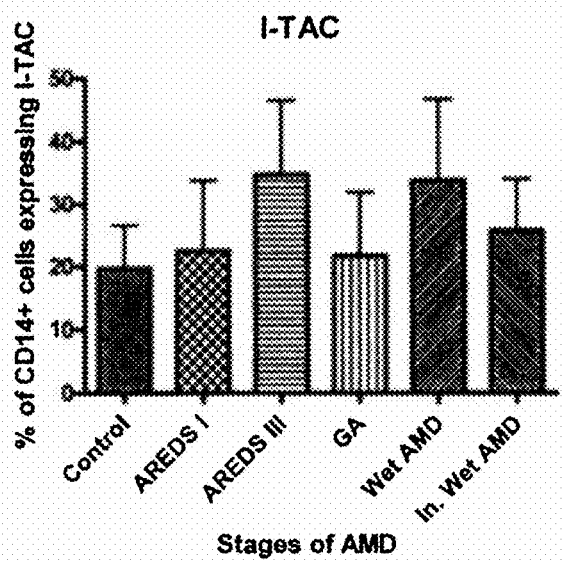

Flow cytometric analysis for expression of these cytokines was performed on peripheral leukocytes freshly collected from subjects with various stages of AMD including active wet AMD, and inactive wet AMD (individuals successfully treated with intravitreal Lucentis™ (ranibizumab; anti-VEGF Fab) or Avastin™ (bevasizumab; humanized anti-VEGF antibody) and deemed to have inactive disease based on clinical and OCT findings). These chemokines were significantly expressed in circulating $CD14^+$ cells (monocytes/macrophages), and significantly less on T and B cell populations. FIGS. 6A, 6B and 6C show that the expression pattern of all 3 chemokines is similar and is elevated in subjects with AMD over control subjects as early as AREDS stage 1 (early AMD). It is also interesting that the levels of all 3 chemokines diminished as after anti-VEGF treatment.

IP-10 in particular is associated with chronic systemic diseases, and its association with AMD implicates a role for chronic systemic inflammation. To test this hypothesis, we examined whether there were any differences between AMD and non-AMD subjects with respect to systemic IP-10 production. Flow cytometry of the blood leukocyte fraction showed that 41.15% vs. 4.75% of circulating $CD14^+$ monocytes expressed IP-10 in AREDS stage 3 vs. control subjects.

Figure 7:
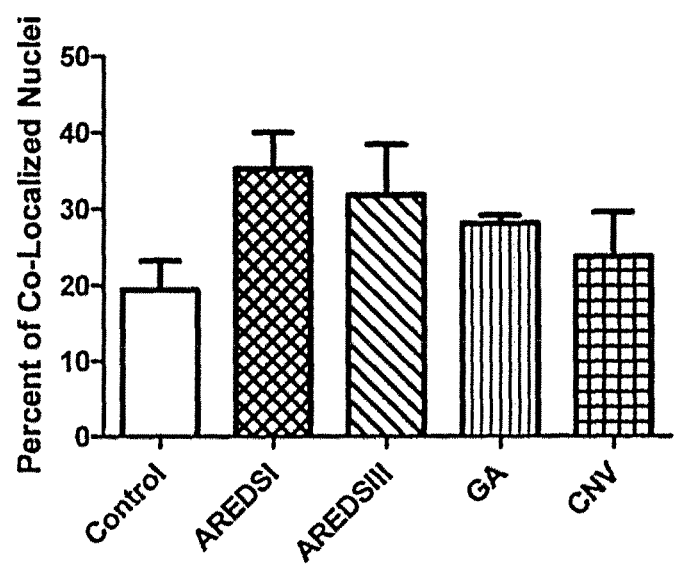
FIG. 7 is a bar graph depicting and correlating the expression of IP-10 in splenic specimens matched to various stages of AMD as shown.

Additionally, spleen and eye specimens were collected from autopsy donors and matched to their respective stage of AMD. Immunohistochemistry was used identify the number of spleen cells that expressed IP-10. Spleen samples showed increased expression of IP-10 in spleen leukocytes around the marginal zone. See FIG. 7 where spleen specimens matched to the stage of AMD collected from autopsy donors show increased expression of IP-10 in splenic lymphocytes as early as early stage AMD (equivalent to AREDS 1).

A level of an AMD biomarker, such as IP-10 and eotaxin are obtained by any art-recognized method. Typically, the level of the marker is measured from a sample of body fluid such as, but not restricted to blood serum.

A number of risk factors are associated with an increased risk of development of AMD. In some embodiments, the risk factor is a family history of AMD, the absence or presence of a genetic marker, increase age, smoking, and obesity. In some embodiments, a risk factor is a level of an AMD biomarker, e.g., IP-10 and eotaxin as described herein.

In some embodiments, the methods include using a subject's serum levels of IP-10 or eotaxin to predict which subject will be most likely to respond to treatment with a therapeutic agent.

Other embodiments are within the scope and spirit of the invention. It will be recognized by a person of ordinary skill in the art that various components of the examples described herein can be interchanged and/or substituted with various components in other examples, and that other modifications may be possible. To the extent that any of the material incorporated by reference herein conflicts with the terms of the present disclosure, the present disclosure is intended to be controlling.

Further, while the description above refers to the invention, the description may include more than one invention.

What is claimed is:

1. A method comprising:
treating dry AMD (age-related macular degeneration) in a subject by administering to said subject a composition that inhibits an activity of IP-10 (interferon-gamma inducible protein-10) by reducing a level of IP-10 present in the subject after administration of the composition relative to a level of IP-10 present in the subject prior to the administration of the composition, wherein the composition comprises one of a solubilized receptor that binds circulating IP-10, a CXCR3 receptor antagonist or a neutralizing antibody.

2. The method of claim 1, wherein said composition is administered intravenously, subcutaneously, or orally.

3. The method of claim 1, wherein said composition is administered locally, topically, intraocularly, periburlbarly, or intravitreally.

4. The method of claim 1, wherein when the composition comprises the CXCR3 receptor antagonist, the CXCR3 receptor antagonist is selected from the group consisting of NSC651016, LMP420, AZD3778, T0906487, AMG487, TAK779, and NBI-74330.

5. The method of claim 1, wherein said method further comprises administering to said subject a second composition that inhibits an activity of eotaxin.

6. A method, comprising:
   treating dry AMD (age-related macular degeneration) in a subject having antibodies at or above an age-related eye disease study (AREDS) stage one by administering to said subject a composition that inhibits an activity of IP-10 (interferon-gamma inducible protein-10) by reducing a level of IP-10 present in the subject after administration of the composition relative to a level of IP-10 present in the subject prior to the administration of the composition wherein the composition comprises one of a solubilized receptor that binds circulating IP-10, a CXCR3 receptor antagonist or a neutralizing antibody.

* * * * *